United States Patent [19]

Menz et al.

[11] Patent Number: 5,284,646

[45] Date of Patent: * Feb. 8, 1994

[54] HEPATOCYTE SPECIFIC RECEPTOR MEDIATED ENDOCYTOSIS TYPE MAGNETIC RESONANCE IMAGING CONTRAST AGENTS

[75] Inventors: Edward T. Menz, Quincy, Mass.; Jeffrey M. Rothenberg, Gary, Ind.; Ernest V. Groman, Brookline, Mass.; Lee Josephson, Arlington, Mass.

[73] Assignee: Advanced Magnetics Inc., Cambridge, Mass.

[*] Notice: The portion of the term of this patent subsequent to Sep. 13, 2005 has been disclaimed.

[21] Appl. No.: 771,876

[22] Filed: Oct. 3, 1991

Related U.S. Application Data

[63] Continuation of Ser. No. 384,991, Jul. 2, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^5$ ............... G01N 24/08; A61K 37/10
[52] U.S. Cl. .................... 424/9; 424/646; 424/648; 514/8; 514/54; 514/57; 514/60; 423/633; 128/653.4
[58] Field of Search .......... 424/9, 5, 646, 648; 436/173, 806; 514/54, 57, 60, 8; 128/653.4, 654; 423/633

[56] References Cited

U.S. PATENT DOCUMENTS 3,325,473 6/1967 Herrick et al. .
3,337,526 8/1967 Adams .

(List continued on next page.)

FOREIGN PATENT DOCUMENTS 0184899 6/1986 European Pat. Off. .
0186947 7/1986 European Pat. Off. .

(List continued on next page.)

OTHER PUBLICATIONS

Balter, S. "An Introduction to the Physics of Magnetic Resonance Imaging," *RadioGraphics* 7(2):371-383 (1987).

(List continued on next page.)

*Primary Examiner*—Allen J. Robinson
*Assistant Examiner*—Gary E. Hollinden
*Attorney, Agent, or Firm*—Pennie & Edmonds

[57] ABSTRACT

A new class of magnetic resonance (MR) contrast agents are described whose in vivo biodistribution is based upon the ability of certain cells to recognize and internalize macromolecules, including the MR contrast agents of the present invention, via a process which substantially involves receptor mediated endocytosis. The RME-type MR contrast agents described herein comprised of biodegradable superparamagnetic metal oxides associated with a variety of macromolecular species, including but not limited to, serum proteins, hormones, asialoglycoproteins, galactose-terminal species, polysaccharides, arabinogalactan, or conjugates of these molecules with other polymeric substances such as a poly(organosilane) and dextran. One of the advantages of these MR contrast agents is that they may be selectively directed to those cells which bear receptors for a particular macromolecule or ligand and are capable of undergoing receptor mediated endocytosis. An MR contrast agent prepared from biodegradable superparamagnetic iron oxide and asialofetuin, or more preferably arabinogalactan, for example, is selectively localized in the hepatocytes of the liver with no significant accumulation in the spleen. An MR experiment which can be carried out shortly after administration to the subject of the contrast agents of the invention can thus provide a method for obtaining an enhanced MR image, as well as valuable information regarding the functional or metabolic state of the organ or tissue under examination. Preparative methods, biodistribution data, and time function MR images are further provided.

27 Claims, 5 Drawing Sheets

U.S. PATENT DOCUMENTS

| | | |
|---|---|---|
| 3,509,126 | 4/1970 | Dahl. |
| 4,554,088 | 11/1985 | Whitehead et al.. |
| 4,637,929 | 1/1987 | Quay. |
| 4,639,365 | 1/1987 | Sherry. |
| 4,647,447 | 3/1987 | Gries ................................. 128/654 |
| 4,675,173 | 6/1987 | Widder ............................. 128/654 |
| 4,770,183 | 9/1988 | Groman ............................. 600/12 |
| 4,804,529 | 2/1989 | Bardy et al. ....................... 424/9 |
| 4,822,594 | 4/1989 | Gibby ................................. 424/9 |
| 4,827,945 | 5/1989 | Groman ............................. 600/12 |
| 4,859,449 | 8/1989 | Mattes ............................... 424/9 |
| 5,032,678 | 7/1991 | Washino et al. .................. 534/14 |

FOREIGN PATENT DOCUMENTS

| | | |
|---|---|---|
| 0210043 | 1/1987 | European Pat. Off.. |
| 0186616 | 9/1990 | European Pat. Off.. |
| 3443251A1 | 11/1984 | Fed. Rep. of Germany. |
| 3508000A1 | 3/1985 | Fed. Rep. of Germany. |
| 85/02772 | 7/1985 | PCT Int'l Appl.. |
| 85/04330 | 10/1985 | PCT Int'l Appl.. |
| 85/05554 | 12/1985 | PCT Int'l Appl.. |
| 86/06605 | 11/1986 | PCT Int'l Appl.. |

OTHER PUBLICATIONS

Fullerton, G. D. "Magnetic Resonance Imaging Signal Concepts," *RadioGraphics* 7(3):579–596 (1987).

Runge, V. M. et al. "The Use of Gd DTPA as a Perfusion Agent and Marker of Blood-Brain Barrier Disruption," *Magnetic Resonance Imaging* 3:45–55 (1985).

Renshaw, P. F. et al., "Immunospecific NMR Contrast Agents," *Magnetic Resonance Imaging* 4:351–357 (1986).

Lauffer, R. B. "Paramagnetic Metal Complexes as Water Proton Relaxation Agents for NMR Imaging: Theory and Design," *Chem. Rev.* 87:901–927 (1987).

Helenius, A. et al. "Endosomes," *TIBS* 8:245–249 (1983).

Pastan, I. et al. "Receptor-Mediated Endocytosis: Coated Pits, Receptosomes and the Golgi," *TIBS* 8:250–254 (1983).

Steinman, R. M. et al. "Endocytosis and the Recycling of Plasma Membrane," *J. Cell Biol.* 96:1–27 (1983).

Wileman, T. et al. "Receptor-Mediated Endocytosis," *Biochem. J.* 232:1–14 (1985).

Raff, M. et al. "Self Regulation of Membrane Receptors," *Nature* 259(25):265–266 (1976).

Jacobs, S. et al. "Current Concepts: Cell Receptors in Disease," *New Engl. J. Med.* 297(25):1383–1386 (1977).

Anderson, R. G. W. et al. "Role of the Coated Endocytic Vesicle in the Uptake of Receptor-Bound Low Density Lipoprotein in Human Fibroblasts," *Cell* 10:351–364 (1977).

Murray, G. J. "Mannose 6-Phosphate Receptor-Mediated Uptake of Modified Low Density Lipoprotein Results in Down Regulation of Hydroxymethylglutaryl-CoA Reductase in Normal and Familial Hypercholesterolemic Fibroblasts," *J. Biol. Chem.* 255(24):11942–11948 (1980).

Pastan, I. H. et al. "Journey to the Center of the Cell: Role of the Receptosome," *Science* 214:504–509 (1981).

Sando, G. N. "p-Isothiocyanatophenyl 6-Phospho-α-D-mannopyranoside Coupled to Albumin. A Model Compound Recognized by the Fibroblast Lysosomal Enzyme Uptake System. 1. Chemical Synthesis and Characterization," *Biochem.* 19:3850–3855 (1980).

Goldstein et al. "The Low-Density Lipoprotein Pathway and Its Relation to Atherosclerosis," *Ann. Rev. Biochem* 46:897–930 (1977).

Harding, C. et al. "Receptor-Mediated Endocytosis of Transferrin and Recycling of the Transferrin Receptor in Rat Reticulocytes," *J. Cell Biol.* 97:329–339 (1983).

Ward, J. H. "The Structure, Function, and Regulation of Transferrin Receptors," *Invest. Radiol.* 22:74–83 (1987).

Larson, S. M. "Factors Determining Tumor Affinity for Gallium-67 Citrate," *Radiopharmaceuticals-Structure, Activity Relationships*, pp. 167–181 (Spencer, R. P. ed. 1981).

Lee, Y. C. et al. "Neoglycoproteins as Probes for Binding and Cellular Uptake of Glycoconjugates," *The Glycoconjugates*, vol. IV, part B, section 3 (Horowitz, M. I. ed. 1982).

Schwartz, A. L. et al. "Characterization of the Asialoglycoprotein Receptor in a Continuous Hepatoma Line," *J. Biol. Chem.* 256(17):8878–8881 (1981).

Stockert, R. J. et al. "Endocytosis of Glycoproteins," *The Liver: Biology and Pathobiology*, ch. 12 (Arias, I., Popper, H.; Schachter, D.; and Shafritz, D. A., eds.) (1982).

Gambhir, K. K. et al. "Insulin Radioreceptor Assay for Human Erythrocytes," *Clin. Chem.* 23(9):1590–1595 (1977).

Beuth, J. et al. "Inhibition of Liver Metastasis in Mice by Blocking Hepatocyte Lectins with Arabinogalactan Infusions and D-galactose," *J. Cancer Res. Clin. Oncol.* 113:51–55 (1987).

Anderson, R. G. W. et al. "Localization of Low Density Lipoprotein Receptors on Plasma Membrane of Normal Human Fibroblasts and Their Absence in Cells from a Familial Hypercholesterolemia Homozygote," *PNAS USA* 73(7):2434–2438 (1976).

Vera, D. R. et al. "Technetium-99m Galactosyl-Neoglycoalbumin: Preparation and Preclinical Studies," *J. Nucl. Med.* 26(10):1157–1167 (1985).

Neutra, M. R. "Intracellular Transport of Transferrin- -and Asialoorosomucoid-Colloidal Gold Conjugates to Lysosomes after Receptor-Mediated Endocytosis," *J. Histochem. and Cytochem.* 33(11):1134–1144 (1985).

Handley, D. A. "Colloidal Gold-Low Density Lipoprotein Conjugates as Membrane Receptor Probes," *PNAS USA* 78(1):368–371 (1981).

Ohnisi, S-I, et al. "Role of Endosomes in Endocytic Response of Cells," *Studia Biophysica* 110:123:126 (1985).

Sato, S. B. et al. "A Novel Method for Isolating Spe- (List continued on next page.)

OTHER PUBLICATIONS cific Endocytic Vesicles Using Very Fine Ferrite Particles Coated with Biological Ligands and the High-Gradient Magnetic Separation Technique," *J. Biochem.* 100:1481–1492 (1986).

Wu, G. et al. "A Hepatocyte-Directed Contrast Agent For Magnetic Resonance Imaging Of Hepatic Tumors," *Hepatology* 8(5):1253 (1988) (abstract 140).

Lee, Y. C. et al. "2-Imino-2-Methoxyethyl 1-Thioglycosides: New Reagents for Attaching Sugars to Proteins," *Biochem.* 15(18):3956–3963 (1976).

Vera, D. R. et al. "Tc-99m Galactosyl-Neoglycoalbumin: In Vitro Characterization of Receptor-Mediated Binding," *J. Nucl. Med.* 25(7):779–787 (1970).

Dubois et al. "Colorimetric Method for Determination of Sugars and Related Substances," *Anal. Chem.* 28:350–356 (1956).

Kitigawa, T. et al. "Enzyme Immunoassay of Blasticidin S with High Sensitivity: A New and Convenient Method for Preparation of Immunogenic (Hapten-Protein) Conjugates," *J. Biochem.* 92(2):585–590 (1982).

Gray, G. R. "The Direct Coupling of Oligosaccharides to Proteins and Derivatized Gels," *Arch. of Biochem. and Biophys.* 163:426–428 (1974).

Spiro, R. G. "Studies on the Monosaccharide Sequence of the Serum Glycoprotein Fetuin," *J. Biol. Chem.* 237(3):646–652 (1962).

Warren, L., "The Thiobarbituric Acid Assay of Sialic Acid," *J. Biol. Chem.* 234(8):1971–1975 (1959).

Stark, D. D. et al. "Magnetic Resonance Imaging of Cavernous Hemangioma of the Liver: Tissue-Specific Characterization," *AJR* 145:213–220 (1985).

Weissieder, R. et al. "Superparamagnetic Iron Oxide: Pharmacokinetics and Toxicity," *AJR* 152:167–173 (1989).

Bolton, A. E. et al. "The Labelling of Proteins to High Specific Radioactivities by Conjugation to a $^{125}$I-Containing Acylating Agent," *Biochem. J.* 133:529–539 (1973).

Greenwood, G. C. et al. "The Preparation of $^{131}$I-Labelled Human Growth Hormone of High Specific Radioactivity," *Biochem. J.* 89:114–123 (1963).

Shirley, C. C. "Regularity within the Molecular Structure of Arabingaloctan from Western Larch (Larix accidentalis)," *Carbohydrate Research* 64:C1–C2 (1978).

*Stractan Catalogue* published by Champion International Corporation (Oct. 1988).

HEPATOCYTE SPECIFIC RECEPTOR MEDIATED ENDOCYTOSIS TYPE MAGNETIC RESONANCE IMAGING CONTRAST AGENTS

This application is a continuation of prior co-pending U.S. application Ser. No. 07/384,991, filed Jul. 2, 1989, now abandoned, which, in turn, is a continuation-in-part of U.S. application Ser. No. 07/228,640, filed Aug. 4, 1988, now abandoned, which, in turn, is a continuation-in-part of U.S. application Ser. No. 07/067,586, filed Jun. 26, 1987, now U.S. Pat. No. 4,827,945, which, in turn, is a continuation-in-part of U.S. application Ser. No. 06/882,044, filed Jul. 3, 1986, now U.S. Pat. No. 4,770,183. The disclosures of all of the above are incorporated herein by reference.

1. FIELD OF THE INVENTION

The present invention relates to the synthesis and use of materials in magnetic resonance imaging. In particular, the compositions of the present invention serve as contrast agents for the enhancement of magnetic resonance (MR) images. The present invention describes a class of MR contrast agents which are directed to specific cells of the body based on the ability of these cells to perform receptor mediated endocytosis. MR agents whose biodistribution is based on receptor mediated endocytosis can enhance the general level of anatomical detail obtained with MR images both between different tissues or within a single tissue. In addition, because receptor mediated endocytosis is a metabolically regulated process, the extent of contrast agent uptake can provide information on the metabolic function of tissue volumes visualized with the MR imaging technique. In particular, the preparation of biodegradable superparamagnetic receptor mediated endocytosis type MR contrast agents is described. The in vivo utility of these contrast agents in MR techniques is demonstrated.

2. BACKGROUND OF THE INVENTION

2.1. Magnetic Resonance Imaging

In magnetic resonance imaging (MRI) an image of an organ or tissue is obtained by placing a subject in a strong magnetic field and observing the interactions between the magnetic spins of the protons and radiofrequency electromagnetic radiation. (For a review of MR imaging technique see Balter, S. *RadioGraphics* 1987, 7(2) 371-383; Fullerton, G. D. *RadioGraphics* 1987, 7(3), 579-596). Two parameters termed proton relaxation times are of primary importance in the generation of the image. They are called $T_1$ (also called the spin-lattice or longitudinal relaxation time) and $T_2$ (the spin-spin or transverse relaxation time). $T_1$ and $T_2$ depend on the chemical and physical environment of protons in various organs or tissues.

The utility of MR imaging techniques in the characterization and differentiation of pathologic from healthy tissues is most easily demonstrated in cases where divergent relaxation times occur within a region of interest. For example in cerebral tissue the protons of the cerebral spinal fluid have far different relaxation times from neural tissue and the resulting MR images are of high contrast.

In other instances the image produced may lack definition and clarity due to a similarity of the signal from different tissues or different compartments within a tissue. In some cases, the magnitude of these differences is small, limiting the diagnostic effectiveness of MR imaging. Thus, there exists a real need for methods which increase or magnify these differences. One approach to improving image quality is through the use of contrast agents.

2.2. The Use of MR Contrast Agents

The field of MR image enhancement and the use of contrast agents are discussed extensively in applicants' co-pending patent application No. 067,586 which is a continuation-in-part of Applicants' patent application No. 882,044. The teachings and publications cited in these applications are incorporated in the instant application by reference. Presently, MR imaging contrast agents fall broadly under three categories: paramagnetic, ferromagnetic, and hyper- or superparamagnetic. Although a wide array of these substances has been investigated for their ability to serve as MR contrast agents, only a small fraction of the material so far reported will prove to have the clinical efficacy and margin of safety required for use in humans.

European Patent Application No. 0 186 616, for example, discloses a whole host of double metal oxide/hydroxide particles for use in diagnostic techniques, including "nmr-diagnosis." Many combinations of metals, of both divalent and trivalent oxidation states, are used along with a wide range of "physiological compatible complex former[s]", including polysaccharides, proteins, carboxylic acids, synthetic polymers, and even zeolites. This European Application is related to the published German patent Application DE 3443251A1, whose disclosures are much more limited. However, the processes and materials disclosed in these preceding foreign applications would not be expected to demonstrate any tissue specificity, and in particular no specificity for hepatocytes.

The earliest MR contrast agents developed include paramagnetic chelates which can alter both $T_1$ and $T_2$ and can be used to visualize the vascular compartment. The most studied compound of this class is a gadolinium chelate, Gd-DTPA, which has proven useful in the imaging of the brain by virtue of its ability to delineate regions where the blood brain barrier has broken down (See, Runge et al., *Mag. Res. Imag.* 1985, 3, 43-55; U.S. Pat. No. 4,647,447). A wide range of paramagnetic iron chelates are also listed in European Patent Application No. 0 186 947, PCT Application WO 85/0554, PCT Application WO 86/06605, European Patent Application No. 0 210 043, and U.S. patent application Nos. 4,639,365 and 4,637,929. These paramagnetic metal chelates are used primarily as intravascular MR contrast agents and have limited utility in imaging organs and tissues of the reticuloendothelial system (RES).

For visualizing parts of the reticuloendothelial system, MR contrast agents based on iron oxides have been developed. These RES-type MR contrast agents are not particularly tissue-specific because they are picked up by the phagocytic cells of the RES present primarily in the liver, spleen, lymphoid system, and the bone marrow. A variety of the magnetic particles can be used because the function of the RES is to remove dead cells, bacteria, and other particulate material from circulation (see U.S. Pat. No. 4,675,173, PCT Applications WO 85/04330 and WO 85/02772, and European Patent Application 0 184 899). Most of these RES-type MR contrast agents employ ferromagnetic materials, but the superparamagnetic materials described by the applicants in their above-referenced co-pending U.S. applications are highly preferred.

Still other types of MR contrast agents include immunodirectable materials. This work was spurred by the ability of radiolabeled antibodies to serve as in vivo diagnostic agents (see Renshaw, P. F. et al. *Mag. Res.* 1986, 4, 351-357). Because some antigens are found only on specific types of cells, immunodirectable MR contrast agents might appear to be an attractive approach to the development of tissue-specific MR contrast agents. There are limitations to antibody-directed MR contrast agents, however. In particular only a limited number of fixed cell surface antigens exist in a specific tissue. As a result only a small proportion, typically only a few percent, of the immunodirectable MR contrast agent administered to the subject become bound to the target cells. A comprehensive review of approaches to MR contrast agent development has recently been compiled (Lauffer, R. B. *Chem. Rev.* 1987, 87, 901-927).

2.3. Ligand Binding and Internalization in Cells

The mechanistic pathway for macromolecule recognition, binding, and internalization into the intracellular compartment is a subject of intense research in cell biology. Most review articles describing endocytosis and related processes for the uptake of extracellular material also discuss the structures of the vacuolar apparatus which take part in the internalization (See, for example, Steinman, R. M. et al., *J. Cell Biol.* 1983, 96, 1-27; Wileman, T. et al., *Biochem. J.* 1985, 232 1-14; Helenius, A. et al., *Trends Biochem. Sci.* 1983, 8 245-249; Pastan, I. H. and Willingham, M. C., *Ibid.* 1983, 8, 250-254)

Investigators in the field agree that the assimilation of physiologically significant molecules such as nutrients, hormones, enzymes, virions, toxins, and various types of proteins begins with the initial binding of the macromolecule or ligand to specific receptors which are mobile and randomly distributed on the cell membrane surface. These ligand-receptor complexes rapidly accumulate in specialized regions of the membrane termed coated pits. From this stage, the receptor-mediated endocytosis (RME) proceeds to the formation of smooth-walled vesicles which allow entry of the concentrated ligand-receptor complexes into the cell. These vesicles, often referred to as "endosomes" or "receptosomes," may fuse together or combine with larger vesicles. Subsequently, the internal pH of these endosomes decrease by the action of proton pumps, changing the conformation of the receptor and/or ligand. The result is the release of the ligand and the formation of separate receptor-containing vesicles and ligand-containing ones. In some cases, the receptor-bearing vesicles are delivered to the cell membrane where they are released and "recycled" for additional use. In others, the resulting vesicles, along with the internalized ligand, are delivered to and fused with lysosomes where the eventual breakdown likely takes place.

A feature of RME is that it is subject to regulation which reflects the metabolism of the cell. The ability of cells to upregulate (increase RME) or downregulate (decrease RME) is a sensitive indicator of their function. For a discussion of the importance of RME regulation in medicine, see Jacobs and Cuatrecasas, *New Engl. J. Med.* 1977, 297, 1383 and *Nature* 1976, 259, 265. A wide variety of molecules are internalized by RME, and for many of these substrates the requisite receptor is found in selected cells or in selected tissues. Thus, for the study of fibroblastic tissue, LDL, EGF, or mannose 6-phosphate glycoproteins are useful (See, for example, Pastan, I. H. and Willingham, M. C., *Science* 1981, 214, 504-509; Anderson, R. G. W. et al., *Cell* 1977, 10, 351-364; Murray, G. I. and Neville, Jr., D. M., *J. Biol. Chem.* 1980, 255, 11942-11948; Sando, G. N. and Karson, E. M., *Biochem.* 1980, 19, 3850-3855). In addition, a receptor for LDL mediates removal of cholesterol from plasma. Alterations in LDL receptor activity may be correlated with elevated serum cholesterol and with the development of atherosclerosis (See, Goldstein and Brown, *Ann. Rev. Biochem.* 1977, 46, 897).

Transferrin receptors are located in a number of cell types but particularly in maturing erythroblasts and reticulocytes of the bone marrow (See, Ward, J. H., *Invest. Radiol.* 1987, 22, 74-83; Harding, E. et al., *J. Cell Biol.* 1983, 97, 329-339). Rapidly dividing cells (e.g. tumor cells) have increased transferrin receptor activity and sequester $^{67}$Ga after the radioactive material has bound transferrin. (Larson, S. M. in "Radiopharmaceuticals—Structure Activity Relationships," Spencer, R. P. ed, (Grune and Stratton, 1981), pp. 167-181)).

Removal of a terminal sialic acid from glycoproteins often exposes a galactose. This terminal galactose of the carbohydrate chain is recognized by a receptor on hepatocytes (Lee, Y. C. and Lee, R. T. in "The Glycoconjugates," Vol. 4, pp. 57-83, M. I. Horowitz, ed. (N.Y., 1982)). The asialoglycoprotein receptor withdraws a variety of molecules with terminal galactose from circulation and internalizes them within vacuoles of hepatocytes. This receptor characteristically disappears when hepatocytes are transformed to hepatoma cell (Schwartz, et al., *J. Biol. Chem.* 1981, 256, 8878-8881) or in rapidly dividing or regenerating hepatocytes (Stockert, R. J. and Morell, A. G. in "The Liver: Biology and Pathobiology", pp. 205-217, I. Arias, H. Popper, D. Schacter and D. A. Shafritz eds. (N.Y., 1982)). The asialoglycoprotein receptor is therefore an excellent example of RME whose function reflects cell metabolism. Of course, the insulin receptor, responsible for regulating the diverse activities of the hormone is of great importance in the pathogenesis of obesity and diabetes (See, Gambhir et al., *Clin. Chem.* 1977, 23, 1590).

Very recently, research carried out by Beuth, J. et al., *Cancer Res. Clin. Oncol.* 1987, 113, 51-55, showed that liver metastasis in mice can be inhibited by blocking hepatocyte lectins with infusions of arabinogalactan or D-galactose. Surprisingly, other galactans were found by these workers to be ineffective liver metastatis inhibitors.

Interestingly, larger protein-protein conjugates, metal-neoglycoalbumin adducts, ternary, or higher order compositions like ferrite-BSA-asialofetuin (AsF) are all effectively bound by the surface receptors of their corresponding cell types. Thus, LDL-ferritin conjugates are useful in studies comparing normal fibroblasts with cells from a familial hypercholesterolemia homozygote (Anderson, R. G. W. et al., *Proc. Natl. Acad. Sci. USA* 1976, 73, 2434-2438 ). In vivo animal studies have shown the high liver specificity of a radioisotope preparation containing $^{99m}$Tc-neoglycoalbumin (Vera, D. R. et al., *J. Nucl. Med.* 1985, 26, 1157-1167). Asialoorosomucoid-gold and transferrin-gold complexes have been studied (Neutra, M. R. et al., *J. Hist. and Cyto.* 1985, 33(11), 1134). Also, conjugates comprised of LDL adsorbed onto colloidal gold are stable probes for fibroblast receptors (Handley, D. A. et al., *Proc. Natl. Acad. Sci. USA* 1981, 78, 368-371). And magnetic preparations using commercial ferrite coated with BSA-AsF are alleged to be useful in the magnetic isolation of murine hepatic endosomes (Sato, S. B. et al., *Studia Biophysica* 1985, 110, 123-126; *J. Biochem.* 1986, 100, 1481-1492).

None of the complexes above have been directed to the preparation of biodegradable superparamagnetic RME-type MR contrast agents. In particular, labeled arabinogalactan species have not been described. Such tissue directable materials could serve as the basis for a diagnostic technique which provides valuable anatomical information, delineating inter alia the extent of injury or recovery of a given organ or tissue.

3. SUMMARY OF THE INVENTION

The present invention provides a new class of MR contrast agents and a method which uses these contrast agents to enhance the quality of MR images. The contrast agents of the invention are distributed in vivo to selected organs or tissues of the subject by a cell recognition and internalization pathway which substantially involves a process known as receptor-mediated endocytosis (RME). These RME-type MR contrast agents are comprised of biodegradable superparamagnetic metal oxides which are associated with selected ligands that are recognized by certain cell receptors. In one embodiment of the invention, a galactose-terminal glycoprotein is labeled with the superparamagnetic metal oxide. Such a contrast agent, when administered parenterally into rats exhibits a marked selectivity for the hepatocytes of the liver at the expense of other organs and tissues of the reticuloendothelial system (RES).

In another embodiment of the present invention a composition of matter is provided which is (i) comprised of arabinogalactan and a diagnostic label, and (ii) selectively recognized and internalized by hepatocytes of the liver through a process which substantially involves receptor-mediated endocytosis.

In yet another embodiment of the present invention, a method is described for obtaining an enhanced MR image of the liver of an animal subject which comprises (a) administering to such a subject an effective amount of a biodegradable colloidal superparamagnetic contrast agent, alone or in combination with a receptor-blocking agent, in a physiologically acceptable medium, said contrast agent (i) comprising aggregates of individual biodegradable superparamagnetic iron oxide crystals associated with a macromolecular species comprising arabinogalactan, and (ii) being selectively recognized and internalized by hepatocytes of the liver through a process which substantially involves receptor mediated endocytosis; and (b) recording such MR image.

The present invention contemplates other MR agents which are likewise directable to other cells which can recognize and internalize specific compositions by RME.

Because the uptake of these contrast agents is governed by RME, a different biodistribution is obtained compared with existing intravascular or RES-type contrast agents. The use of these RME-type contrast agents according to the methods of the invention affords superior anatomical detail both between different organs or tissues and within different compartments of the same organ or tissue.

It is also an object of the present invention to provide a diagnostic method, based on MR, which affords valuable information drawn directly from the metabolic, physiological, or pathological condition of the organ or tissue under examination.

The invention further contemplates MR contrast agents directable to specific cells by recognition and internalization mechanisms other than RME.

4. BRIEF DESCRIPTION OF THE FIGURES

5. DETAILED DESCRIPTION OF THE INVENTION

Figure 1:
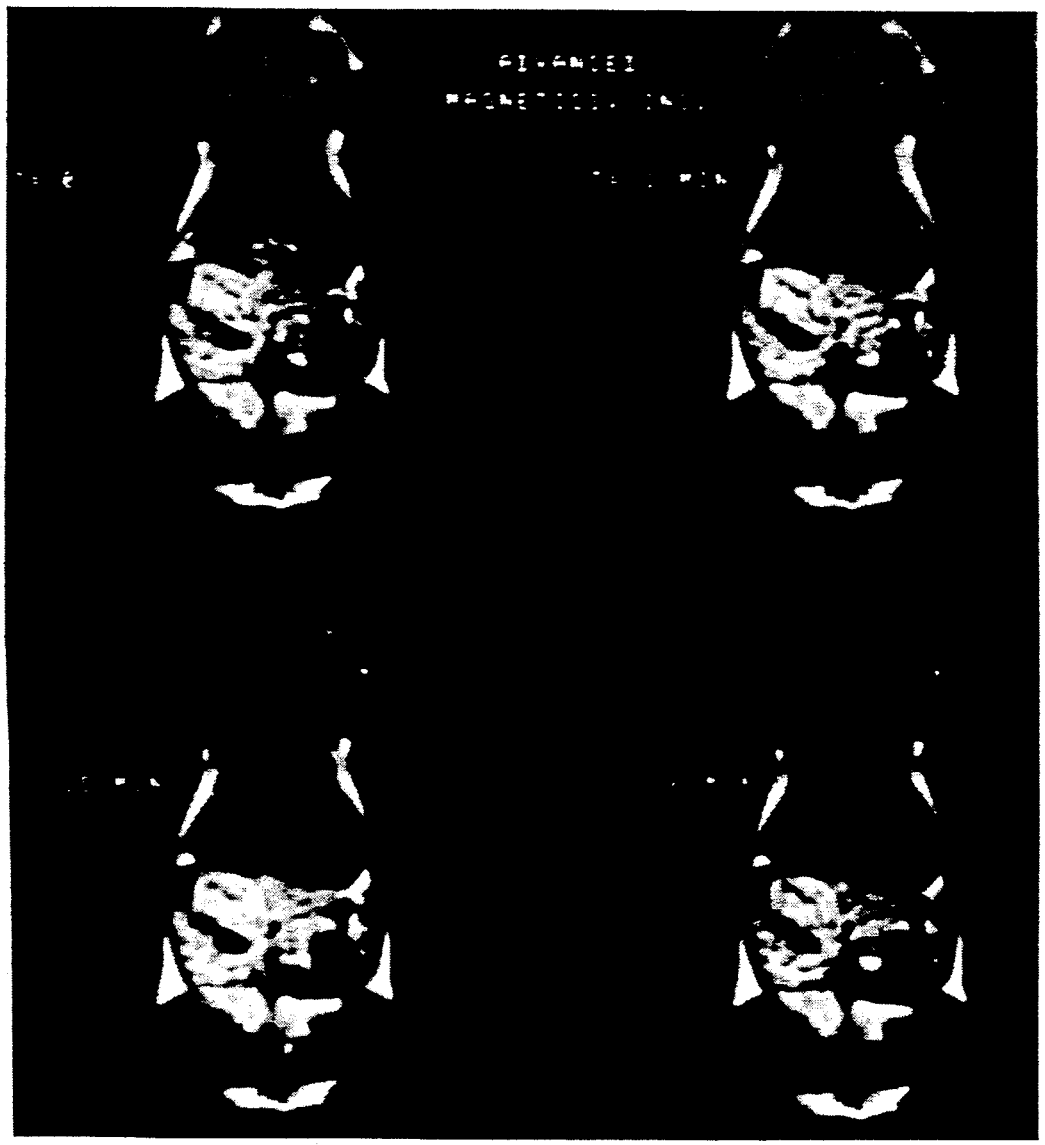
FIG. 1 shows a series of MR images of a rat taken at different times after administration of the RME-type MR contrast agent of the invention.

In common with other types of MR contrast agents, RME-type MR contrast agents can enhance MR images by improving overall contrast (i.e., anatomical detail) both between tissues or within a given tissue. With the RME-type contrast agents, however, such an image may be obtained free from interference from nearby organs or surrounding fluid and employing an optimized dose versus toxicity characteristic of the MR contrast agent. Moreover, the localization and uptake of the RME-type contrast agent, and hence the resulting image, are governed by variations in the rate of RME which is, in turn, a function of the metabolic state or general health of the cell. Therefore, RME-type contrast agents can provide direct information regarding the functional state of the organ or tissue under examination, thereby improving the utility of the MR technique overall.

5.1. Preparation of Receptor-Recognized Ligands

The ligands useful in the instant invention may be synthetic but physiologically tolerable materials and, preferably, comprise natural biomolecules or slightly modified derivatives thereof. These ligands may be simply a mono-, di- or oligosaccharide such as galactose, $\beta$-D-galactopyranosyl-D-galactose, or $\alpha$-D-galactosyl-$\alpha$-D-galactosyl-$\alpha$-D-glucosyl-$\beta$-D-fructose. Other ligands such as polysaccharides, carbohydrates, or polymerizable organosilanes may be used after conjugation or modification with the appropriate macromolecular species. Suitable organosilanes include aminopropyltrimethoxysilane, p-amino-phenyltrimethoxysilane, N-2-aminoethyl-3-aminopropyltrimethoxysilane, n-dodecyltriethoxysilane, and n-hexyltrimethoxysilane. Simple proteins and other macromolecules useful for direct association with the biodegradable superparamagnetic metal oxides described herein are listed in Table I. These maoromolecules, as mentioned, may also be useful in the synthesis of binary, ternary, or higher-order conjugates.

TABLE I

Ligands and Macromolecular Species Useful in Receptor-Mediated Endocytosis (RME) and their Respective Cell Targets[a]

| Ligand | Cell Type | Delivery to Lysosomes |
|---|---|---|
| Low density lipoprotein (LDL) | Fibroblasts | Yes[b] |
| Intrinsic factor | Intestinal epithelium | Probably |
| Transcobalamin II | Many types | Yes |
| Transferrin | Erythroid, Reticulocyte, Macrophages | Probably |
| Phosvitin | Oocytes | No |
| Insulin | Hepatocytes, Monocytes, Adipocytes | Yes |
| Chorionic Gonadotropin | Leydig tumor, Ovarian luteal cells | Yes |
| Chemotactic peptide | Leukocytes | Yes |
| Complement (C3b) | Leukocytes | Probably |
| Epidermal growth factor (EGF) | Fibroblasts | Yes |
| Mouse IgG | Macrophages Lymphocytes | Yes |
| Maternal IgG | Intestinal epithelium | Probably |
| IgA | Leukocytes, Intestinal epithelium | No |
| IgE | Basophils, mast cells | Unknown |
| Galactose-terminal glycoproteins | Hepatocytes | Yes |
| Mannose-terminal glycoproteins | Macrophages, endothelial cells | Yes |
| Man 6-P glycoproteins | Fibroblasts | Yes |
| Acetylated LDL | Macrophages | Yes |
| $\alpha_2$-Macroglobulin ($\alpha_2$M)-protease complexes | Macrophages | Yes |

[a]This list is adapted from Steinman, R. M. et al. J. Cell Biol. 1983, 96, 1–27 and is not comprehensive. This list should not be construed as limiting the embodiments of the invention.

[b]"Delivery to Lysosomes" means that ligand accumulation has been visualized in lysosomes, or that degradation of ligand occurs intracellularly.

Low-density lipoprotein (LDL), transferrin, insulin, and the galactose-terminal glycoproteins are preferred ligands. In a preferred embodiment of the invention, an RME-type MR contrast agent designed to engage the asialoglycoprotein receptor (ASGPR) of hepatocytes is prepared using macromolecular species or conjugates with terminal galactose groups. These galactose groups can be contained in polysaccharides, functionalized dextran or organosilane conjugates, galactose-terminal proteins such as asialofetuin or asialoorosomucoid, or modified albumins called neoglycoalbumins. When employing asialofetuin as a ligand, other serum proteins may be employed in combination with this ligand.

In this fashion a number of specific tissues and organs can be selectively targeted. These "designer" contrast agents should find particular utility in the diagnosis of primary and secondary (metastatic) cancers, especially of the liver, in acute cases of cirrhosis and hepatitis, and in the prognosis of transplanted or traumatized livers. This invention seeks to provide an effective means for monitoring the progress of a given treatment and for examining organ and tissue damage arising from, for example, hereditary abnormalities, malnutrition, exposure to parasitic organisms, infections, harmful drugs, the presence of neoplastic diseases, chronic cirrhosis and hepatitis, or the simple degenerative breakdown of physiological mechanisms within the body.

It is also intended that the compositions used and the methods of the instant invention provide a direct measure of liver function and regional differences in the state of the liver. On the other hand, connective tissues may be examined by the use of LDL, EGF, or Man 6-P-based ligands. In addition, choriocarcinoma cells (pelvic tumors), breast cancer cells, malignant cervical tissues, and high-grade lymphomas may be visualized using MR imaging contrast agents targeted to the transferrin receptor. Other tissues which possess receptors to specific ligands may also be targeted and imaged in a similar manner.

Moreover, by the appropriate choice of ligand, the tissue-specific MR contrast agents may be designed to reside on the surface of the cell membrane for variable lengths of time, from seconds to hours.

Some substrates may be purchased from commercial sources. Hexoses, such as D- or L-galactose, -glucose, or -mannose are available, as are galactosamine, glucosamine, mannosamine hydrochlorides, and D-mannopyranosyl 6-phosphate. The p-aminophenyl derivatives of most hexoses are available also. Likewise, certain oligosaccharides, for example, lactose, maltopolyoses, and $\alpha$-D-galactosyl-$\alpha$-D-galactosyl-$\alpha$-D-glucosyl-$\beta$-D-fructose, may be purchased.

A highly preferred macromolecular species useful in targeting the hepatocytes of the liver is the carbohydrate, arabinogalactan. This galactose-containing carbohydrate is available from commercial sources and may be derivatized, like other carbohydrates, by methods well-known in the art.

Other starting materials may be prepared by adapting methods well known in the art. Some references are provided in the Examples Section of this application, infra.

5.2. Functionalization of Protein End Groups

Proteins may be modified by the functionalization of their end groups. For example, BSA has 59 amino-termini which may serve as nucleophiles for reaction with appropriate electrophilic reagents. Conjugation with appropriate molecules may also be achieved by diazotization (especially useful for derivatizing tyrosine and histidine residues), by the intermediacy of carbodiimides, mixed anhydrides, or the use of glutaraldehyde followed by hydrogenation.

One means of attaching carbohydrate groups to albumins involves the generation of 2-imino-2-methoxyethyl 1-thioglycosides in situ from the cyanomethyl 2,3,4,6-tetra-O-acetyl-1-thioglycoside compounds. For instance, when cyanomethyl 2,3,4,6-tetra-O-acetyl-1-thio-$\beta$-D-galactopyranoside, 1, is treated with a catalytic amount of sodium methoxide in dry methanol, compound 2 is produced. The addition of the appropriate amount of BSA allows for the

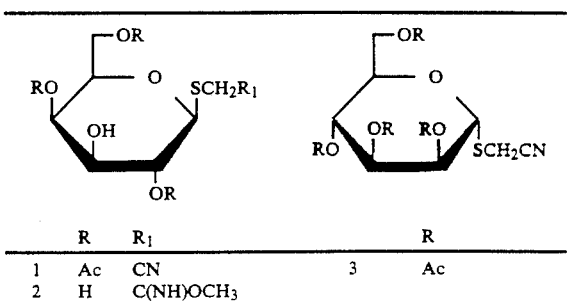

| | R | $R_1$ | | R |
|---|---|---|---|---|
| 1 | Ac | CN | 3 | Ac |
| 2 | H | C(NH)OCH$_3$ | | | functionalization of a predictable number of the amino groups in the albumin (See Section 6.1, under EXAMPLES). The number of glycoside groups in the resulting neoglycoalbumin (NGA) can be determined by colorimetric analysis.

Cross-linking agents may also be employed in the preparation of NGAs. One useful agent is N-(m-maleimidobenzoyloxy)succinimide (MBS). A tetrahydrofuran

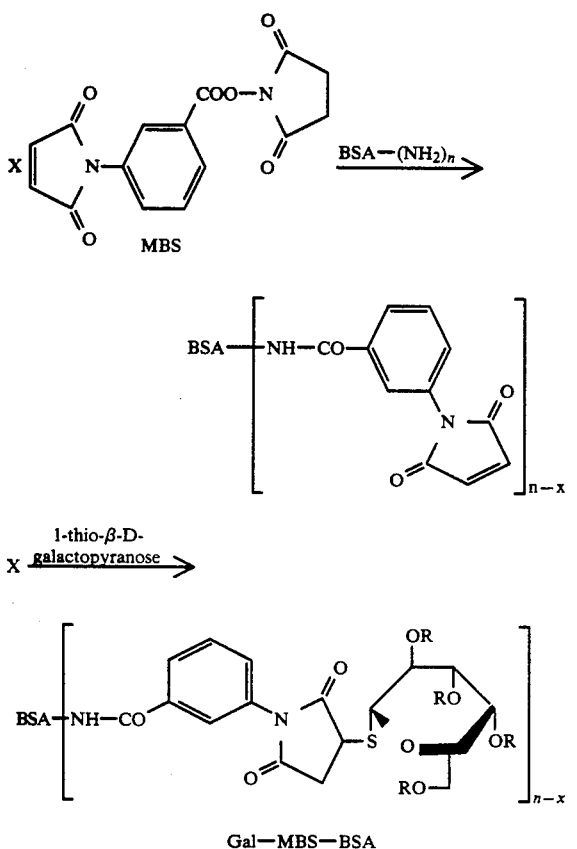

solution of MBS is combined with the desired in neutral buffer. The MBS-BSA adduct is then allowed to react with 1-thio-β-D-galacto-pyranose for a few hours at room temperature.

A convenient but less effective method for producing NGAs involves the direction reaction between the amino groups of BSA and the aldehydic carbon nucleus of lactose. Because only a small proportion of the glucosyl portion of lactose is in the open-chain aldehydic form, very long reaction times are required. Even then, only a few of the amino groups of BSA are derivatized.

In a particular embodiment of the invention, a reactive glycoside derivative derived from compound 4 is used to functionalize BSA. The p-aminophenyl glycoside, 4, is allowed to react with thiophosgene in a dual phase medium of, for example, aqueous bicarbonate buffer-chloroform. The product phenylisothiocyanate is combined with an aqueous solution of BSA and allowed to stand overnight. Purification of the NGA, with a Man 6-P/BSA ratio of about 16, is achieved by chromatography through a Sephadex column.

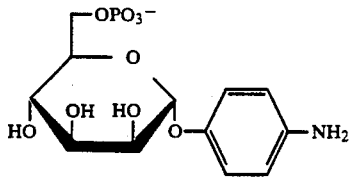

Yet another means of preparing receptor-recognized protein conjugates employs the linking of the "active" (receptor-recognized) protein with a second normally inactive polypeptide. Thus, LDL, transferrin, or galactose-terminal proteins may be covalently attached to BSA using glutaraldehyde and sodium cyanoborohydride. The galactose-terminal proteins may be obtained, in turn, from the enzymatic digestion of the appropriate protein containing a penultimate galactopyranosyl group. For example, neuraminidase is effective in cleaving the terminal sialic acid group in fetuin or orosomucoid to expose the galactopyranosyl end group.

The characterization of the resultant conjugates may be accomplished by traditional chemical analytical methods. For the low molecular weight compounds, chromatography (TLC, GLC, HPLC, etc.) can help establish the purity and homogeneity of the end products. Microanalysis and spectroscopic techniques (e.g., UV/vis, infrared, proton and carbon-13 NMR, or MS) can provide information regarding the elemental composition and structure of the compounds of interest. Similar analytical techniques can apply to the higher molecular weight species and protein fragments. In addition, solution molecular weights can be determined by gel filtration in conjunction with protein standards of known molecular weight. The molecular weight of component or modified protein chains can be estimated using gel electrophoresis. The glycoside/protein ratios can be determined by either a colorimetric technique or by the use of carbon-14 labeled glycoside groups. Additional analytical methods are mentioned in the following sections.

One of the distinct advantages of utilizing contrast agents with ligands which are recognized by cells capable of undergoing RME is that these compositions can be modified substantially and still function effectively according to their design.

5.3. Preparation of Superparamagnetically-Labeled RME-Type MR Contrast Agents The superparamagnetic label is comprised of aggregates of individual biodegradable superparamagnetic metal oxide crystals and is prepared preferably in the hydrated state from a combination of trivalent and divalent metal cationic salts. These superparamagnetic crystals are typically 5–10 nm in diameter, but upon clustering, the resulting aggregates may be as large as 1000 nm. It is important to note that the larger the overall dimension of the aggregate, the higher is the likelihood that these larger particles are removed from the extracellular fluid by phagocytosis. This condition is generally avoided by employing relatively small aggregates, those having volume median diameters (as measured by light scattering) 100 nm or less, preferably 50 nm or less. At these dimensions, the biodistribution of the RME-type contrast agent based upon the recognition and internalization by cells having a particular ligand-sensitive surface receptor is fully exploited.

The metal oxides of the instant invention are capable of being biodegraded in a subject as evidenced by a return of proton relaxation rates of the imaged organ or tissue to pre-administration levels within 30 days of administration.

Most advantageously, the biodegradable superparamagnetic metal oxide is made from iron, but other metals including cobalt, chromium, molybdenum, manganese, nickel, vanadium, tungsten, or copper, to name a few, may be selected. The receptor-recognized ligand or macromolecular species is associated to the metal oxide aggregates by a procedure which preferably precipitates the metal oxides in the presence of the desired ligand species. Hence solutions containing the appropriate amounts of trivalent and divalent metal salts and the selected ligand (mono-, oligo- or polysaccharide, carbohydrate, organosilane, protein, protein conjugate, or a mixture of proteins and other ligands) are combined and treated with aqueous ammonium hydroxide solution.

The dark superparamagnetic composition which forms is collected by centrifugation, resuspended, and subjected to sonication. Excess or unreacted reagents are generally removed by dialysis. The physiologically acceptable carriers or media which can be used in the invention are those generally recognized and known in the art. These carriers may include, but are not limited to, aqueous solutions, saline, buffered solutions, solutions containing polycarboxylic acid salts and the like, or mixtures thereof. The size distribution of the associated particles may be determined by light scattering methods, X-ray diffraction, electron microscopy or other suitable analytical method.

It has further been discovered that heating the freshly precipitated metal oxide composition to a temperature of about 90° C. to about 100° C. provides metal oxide crystal aggregates having smaller volume median diameters as determined by light scattering, while also having a somewhat narrower overall size distribution. This modified procedure, as described further in Section 6.10, provides higher yields of material based on iron and need not be subjected to a sonication step. These "colloidal" metal oxide preparations, like their earlier counterparts, have a maximum overall mean diameter (or volume median diameter) of about 5000 angstroms. Preferably, these aggregates fall below 3000 angstroms, and most preferably, below 1000 angstroms. Of the available macromolecular species, arabinogalactan has been found to give the best results with respect to targeting the hepatocytes of the liver (more, infra).

In fact, arabinogalactan can be modified in any number of ways well known to those of ordinary skill to incorporate any desired "label." Such a "label" may be chosen from any kind of radioisotope, for example, $^{14}C$, $^{3}H$, $^{123}I$, or $^{125}I$. Any radioactive or paramagnetic metal may also be incorporated as a label. Examples of such metallic species may include, but are not limited to, gadolinium, gallium-67, technetium-99, or technetium-99m. Also, and as already mentioned previously, it may be desirable to replace at least part of the divalent iron in a colloidal preparation of biodegradable superparamagnetic iron oxide with other divalent metals, preferably zinc, manganese, or cobalt.

Typically, when synthesizing colloidal contrast agents in which the metal is iron and in which the ligand contains a galactose-terminal moiety, the galactose/iron molar ratio will be not less than about 0.0001 and not greater than about 1.0.

5.4. Determination of the In Vivo Distribution of RME-Type MR Contrast Agents and Their Enhancement of MR Images The superparamagnetically-labeled materials of this invention can be prepared with radioisotopes such as $^{14}C$, $^{123}I$, or $^{125}I$. After the MR agents are administered to test animals, tissue samples can be obtained and the level of radioactivity is measured. Different levels of radioactivity for different tissue samples indicate the relative specificity of the RME-type MR contrast agent for the respective tissues or organs. Methods for the preparation of radiolabeled proteins and peptides are described in the literature and discussed further in the EXAMPLES (Section 6.3).

A more satisfactory approach involves the imaging of the mouse or patient, and the direct determination of proton relaxation times using a magnetic resonance spectrometer. The instrument may be focused on individual organs and tissues and their $T_1$ and/or $T_2$ values are measured readily. A comparison of these values provides a gauge for the specificity of the RME-Type MR contrast agents. The results of these MR experiments provide useful information in and of themselves. If so desired the actual MR image may then be generated as part of the MR experiment.

An image of the organ or tissue under examination can be generated and manipulated with the aid of numerous pulse sequence and data-acquisition techniques. Examples of some of these techniques are listed in Section 6.8. The final result can be dependent on the type of tissue being investigated and the disease state. In the case of hepatocyte directed contrast agents, the number of functioning ASGPRs can be a measure of the condition of the liver. It is regarded, for example, that a characteristic loss of ASGPRs and the corresponding loss of ability to endocytose asialoglycoproteins is associated, generally, with transformed hepatocytes (i.e., hepatoma cells). Less magnetic material is expected to concentrate in the transformed tissue and, therefore, these areas are anticipated to be lighter in shade than the surrounding healthy tissue.

By contrast, cells that utilize a large amount of iron (e.g., developing cells or rapidly-dividing ones) possess a greater number of transferrin receptors. Thus, it may be expected that images of tumorous growths in the region of the bone marrow may appear darker than surrounding untransformed tissue. In this manner, information useful in diagnosing the metabolic state of an organ or tissue may be obtained.

It has been found that a MR contrast agent which is exceptionally selective for the hepatocytes of the liver can be obtained from a colloidal superparamagnetic metal oxide associated with a macromolecular species comprising arabinogalactan, a galactose-containing carbohydrate (See, for example, Beuth, J. et al. in Cancer Res Clin Oncol 1987, 113, 51–55, the disclosures of which are incorporated herein by reference). Administration of this "hepatocyte-specific" MR contrast agent in mice in amounts effective to cause a marked change in the relaxation times of hepatic tissue protons has a negligible effect on the relaxation times of splenic tissue (See, Table V). This specificity has been observed despite the propensity of colloidal superparamagnetic iron oxides to be taken up by the spleen as found for the RES-type MR contrast agents.

The rate of clearance of this HS MR contrast agent from the blood is sensitive to the presence of circulating asialo-(or galactose-terminal)-glycoproteins. As evident from FIG. 4, pre- or co-injection of asialofetuin inhibited the clearance of the contrast agent while the use of fetuin, a non-galactose-terminal glycoprotein, had no effect on the rate of clearance. From this sensitivity to circulating galactose-terminal moieties (D-galactose is also expected to affect the clearance rate of the contrast agent and the observed liver hepatocyte specificity, one may conclude, justifiably, that the contrast agent is being selectively removed from the blood by the asialoglycoprotein receptor of hepatocytes.

It should be pointed out, however, that the interpretation of the blood clearance of a given compound, in terms of hepatic receptor activity, is complicated by the possibility that a slow clearance rate from the blood may reflect not a decreased hepatic receptor activity but a decreased hepatic blood flow. This latter situation arises when a particular compound has a high first pass extraction efficiency; that is, a compound is removed substantially after a single pass through the hepatic capillary bed, with every little of the compound reaching the hepatic receptor sites. conversely, a low first pass extraction efficiency allows hepatic metabolic activity to be the rate-limiting step in the clearance of a compound from the blood, rather than the organ (liver) blood flow.

Although the first pass extraction efficiency of the present HS MR contrast agent is hard to determine, especially with a blood half-life of only 4.9 minutes, there is ample reason to believe that organ blood flow will not be a significant factor in determining the metabolic state of the organ as a function of the contrast agent uptake. First, the dosage used in MR imaging is generally high enough to guarantee that a significant proportion of the administered contrast agent will reach the target receptors. If not, the dosage can be increased particularly because the present preparations are of such low toxicity. Alternatively, receptors in the capillary beds may be competitively bound by pre- or co-administration of receptor-blocking agent. As mentioned previously, such blocking agents may include, but are not limited to galactose, neoglycoalbumin, and other galactose-terminal moieties such as asialofetuin or arabinogalactan itself.

A dose of as little as 20 μmol Fe/kg of the subject rat has been found effective to provide an enhanced MR imgage. This dosage corresponds to 78 mg Fe for a 70 kg man. Furthermore, the toxicity studies undertaken have shown that the $LD_{50}$ of the HS MR contrast agent is at least 1800 μmol/kg rat, providing a safety factor of at least 90. These "coated" superparamagnetic colloids, like their RES-type predecessors, have the metal comprising about 50% of the colloids' mass, with the remainder constituting oxygen and the associated macromolecule. Thus, about 160 mg of the HS MR contrast agent is needed to produce an enhanced image. This dose is markedly less than that (gram quantities) which would be required to effect a similar result using asialoglycoproteins labeled with a paramagnetic metal (See, for example, Wu, G. Y. et al. in *Hepatology* 1988, 8, 1253).

Moreover, further improvements on synthetic technique, MR pulse-sequence methods, and a reduction in the lag time between administration of the contrast agent and actual acquisition of data, may reduce the dosage requirements still further. The pulse sequence employed to record the image presented in FIG. 5, may be described as a mid $T_1$-$T_2$ weighted spin-echo pulse sequence. Highly $T_2$ weighted spin-echo, or gradient echo pulse sequences, have also been used to record the effect of hepatic superparamagnetic iron oxide.

The following examples are meant to illustrate further embodiments of the present invention and should not be construed as limiting its scope or utility in any manner.

6. EXAMPLES

6.1. Amidination of Bovine Serum Albumin (BSA) with 2-Imino-2-Methoxyethyl-1-Thio-β-D-Galacto-Pyranoside (IME-Thiogalactoside, 2). Synthesis of Neoglycoalabumin (NGA)

The cyanomethyl 2,3,4,6-tetra-O-acetyl-1-thio-β-D-galactopyranoside, 1, is prepared by the multistep sequence outlined by Lee, Y. C. et al. *Biochem.* 1976, 15, 3956–3963. Compound 1 is converted to the reactive intermediate, 2-imino-2-methoxyethyl-1-thio-β-D-galactopyranoside (IME-thiogalactoside, 2), by a catalytic amount of sodium methoxide (NaOMe) in methanol. Typically, anhydrous methanol solutions of 1 (0.1M) and NaOMe (0.01M) proceed to about 60% completion after 48 h at 20° C. The volatile components of the reaction mixture are removed under vacuum, and the resulting syrup is added to a freshly prepared 0.25M sodium borate buffer (pH 8.5) containing 20 mg of BSA per mL of solution.

At an incubation temperature of 25° C., the coupling reaction approaches completion within 1 h. The resulting ratio of galactose groups per molecule of albumin (Gal/BSA) can be preselected (within approximately 20%) by utilizing the following linear relationship:

$$\frac{Gal}{BSA} = 4.5 + 0.12\left(\frac{IME}{BSA}\right)$$

where IME/BSA represents the initial molar ratio of 3 to BSA. Up to 44 moles of galactose per mole of albumin can be achieved (See Vera, D. R. et al. *Ibid.* 1984, 25, 779–787), but a ratio of 15–20 galactose groups/albumin is preferred. Unreacted 2 is removed from the NGA product solution by diafiltration (Amicon PM30) with five exchange volumes of isotonic saline. The Gal/BSA ratio is determined by colorimetric analysis as described by Dubois and co-workers, *Anal Chem.* 1956, 28, 350–356.

Mannose-terminated neoglycoalbumin is prepared in a similar fashion using cyanomethyl 2,3,4,6-tetra-O-acetyl-1-thio-α-D-mannopyranoside, 3, as starting material. Other glycoside-terminal NGAs are prepared in the same fashion. Of course, human serum albumin may be used in place of BSA.

6.2. Reaction of BSA with N-(M-Maleimidobenzoyloxy)-Succinimide (MBS). Production of 1-Thiogalactose-Terminal BSA Using a Bifunctional Cross-Linking Agent The ternary adduct thiogalactopyranose-MBS-BSA is produced by a modified procedure based on the work by Kitigawa et al. *J. Biochem.* 1982, 92, 585–590.

A 0.05M sodium phosphate buffer (pH 7.0) solution of BSA (0.5 μmol, 2 mL) is incubated with a tetrahydrofuran solution of MBS (10 μmol, 0.5 mL) at 30° C. for 30 min with occasional stirring. The organic solvent is removed by flushing with nitrogen, and the residual aqueous phase is washed with methylene choride (3×5 mL) to remove unreacted MBS. The resulting aqueous solution of MBS-BSA is combined with an aqueous solution of 1-thio-β-D-galactopyranose (10 μmol, 1 mL), and the reaction mixture is allowed to stand at room temperature for 2-3 h. The product thiogalactopyranose-MBS-BSA is purified by diafiltration or by chromatography through a Sephadex G-100 column. The number of thiogalactopyranose residues per molecule of BSA in the conjugate is determined by the colorimetric method of Dubois (See Section 6.1, supra).

6.3. Reductive Alkylation of BSA Using $^{14}$C-Lactose and Sodium Cyanoborohydride An alternative synthesis of NGA is carried out by adapting the method of Gray, G. R. *Arch. Biochem. Biophys.* 1974, 163, 426-428. The BSA (67 mg), lactose (100 mg, containing 10 μCi of $^{14}$C-lactose), and sodium cyanoborohydride (52 mg) are dissolved in aqueous 0.2M sodium carbonate buffer (5 mL, pH 8.5). After standing for 5 days at room temperature, the excess reagents are removed by diafiltration. Up to about 30 of the lysine residues of BSA are glycosylated by this method as determined by the amount of $^{14}$C-lactose of known specific activity incorporated into the albumin. The Gal/BSA ratio can be adjusted slightly by changing the time, reaction temperature, and/or the pH of the reaction mixture.

6.4. Preparation of p-Isothiocyanatophenyl 6-Phospho-α-D-Mannopyranoside-BSA Conjugates (Man 6-P-BSA)

The p-aminophenyl 6-phospho-α-D-mannopyranoside, 4, is prepared by one of the methods outlined by Sando and Karson, *Biochem.* 1980, 19, 3850-3855. Compound 4 is coupled to BSA by the following procedure:

To a tightly-capped reaction vessel containing a solution of compound 4 (15 μmol) in 1.0 mL of aqueous 0.1M sodium bicarbonate (pH 8) is added, via syringe and with stirring, 0.13M thiophosgene in chloroform (1.0 mL). The reaction is allowed to proceed for 20 min, and afterward the aqueous phase is extracted with fresh chloroform (2×1.5 mL) to remove excess thiophosgene. Residual chloroform is removed from the aqueous reagent solution by brief exposure to a stream of nitrogen. Subsequently, the phenylisothiocyanate solution is combined with 15 mg of BSA (0.22 μmol) dissolved in 1.0 mL of 0.1M NaHCO$_3$-0.15M NaCl (pH 9) buffer and allowed to stand at room temperature for 18 h.

The product mixture is applied to a 1×10 cm Sephadex G-25 column previously equilibrated with 0.1M sodium phosphate-0.15M sodium chloride, pH 6.0. The fractions containing the Man 6-P-BSA are combined and dialyzed against the same phosphate buffer at 4° C. The resulting Man 6-P/BSA ratio in the final conjugate is found to be ca. 16.

The product Man 6-P-BSA neoglycoalbumin can be used directly for the synthesis of superparamagnetic RME-type contrast materials (Section 6.6).

6.5. Preparation of Asialofetuin (AsF) by Enzymatic Digestion of Fetuin

Following the procedure of Spiro, R. G. (*J. Biol. Chem.* 1962, 237, 646-652): Fetuin (0.1 g) is incubated with neuraminidase (1 unit) for several hours at 37° C. in 0.1M calcium chloride. If desired the resulting protein mixture can be further digested by the addition of proteinase K (2 mg) as suggested by Sato and co-workers, *J. Biochem.* 1986, 100, 1481-1492. The desialylated protein is separated from the cleaved sialic acid either by dialysis against distilled water or by chromatography (Dowex 1-X8 resin, 50-100 mesh). The formate form of the Dowex 1 resin retains the sialic acid, and the asialofetuin is recovered from the effluent and washed. The final product can be tested for residual sialic acid by the thiobarbituric assay as described by Warren, L. *J. Biol. Chem.* 1959, 234, 1971-1975.

The AsF may be used directly in the preparation of the superparamagnetic RME-type contrast agents. An AsF-BSA conjugate may also be prepared, if so desired, by the action of glutaraldehyde and subsequent reduction of the linked imine groups by a suitable reducing agent such as sodium cyanoborohydride.

6.6. Synthesis of Superparamagnetic RME-Type MR Contrast Agents

6.6.1. Synthesis of Superparamagnetic Asialofetuin

Into a clean centrifuge tube containing 20 mL of distilled water is added 1.25 mL each of an aqueous solution of asialofetuin (1 mg/mL) and an aqueous solution of bovine serum albumin (1 mg/mL). To the resulting solution is added, simultaneously, 175 μL of an aqueous solution containing 35 mg of ferrous chloride tetrahydrate and 140 μL of an aqueous solution containing 70 mg of ferric chloride hexahydrate. The resulting mixture is vortexed and then made alkaline (pH ~8.5) by the addition of a sufficient amount of aqueous 7.5% ammonium hydroxide solution (ca. 500 μL). The black precipitate which forms is collected by centrifugation (3000 rpm×10 min), and the supernatant is discarded. The pellet is washed by adding aqueous KH$_2$PO$_4$ (pH 7.0, 40 mL), vortexing, and centrifuging the suspension. The washing procedure is repeated a total of three times.

After the third and final wash, the pellet is resuspended once more with the neutral potassium phosphate buffer, transferred to a beaker, and sonicated for about 90-120 sec using a Branson 184 V sonicator probe. Light scattering measurements indicate that the volume median diameter (VMD) of the particles decreases from about 800-1000 nm to about 100 nm (1000 angstroms) during the period of sonication. Furthermore, these particles are generally comprised of one or more individual metal oxide crystals. The technique also indicates that the particles tend to be non-uniform in size. Other techniques for determining the size distribution may also be employed such as electron microscopy. Analysis of the dry weight of the particle indicates the presence of about 5% by weight protein.

As mentioned previously, other macromolecules like transferrin, LDL, insulin, or neoglycoalbumin (NGA) may be used in the procedure. Also, an alternative mode of preparation involves first preparing a superparamagnetic BSA material and then conjugating asialofetuin molecules or other glycoprotein molecules to the associated BSA by a method such as that outlined under Section 6.4. The superparamagnetic conjugates may also be isolated by centrifugation in a discontinuous sucrose density gradient if so desired. (See, Sato and co-workers, *J. Biochem.* 1986, 100, 1481-1492). Optionally, such materials may be filtered through a Nuclearpore membrane of a specified pore diameter.

6.6.2. Preparation of a Superparamagnetic Dextran-Transferrin Conjugate

The following is a modified procedure for the preparation of ultra-small biodegradable superparamagnetic iron oxide to which is conjugated molecules of transferrin.

To an aqueous solution (250 mL) of $FeCl_3 \cdot 6H_2O$ (35 g) and $FeCl_2 \cdot 4H_2O$ (16 g) is added a sufficient amount of aqueous 10% sodium carbonate to bring the pH of the solution to a value of about 2.3. Solid dextran (150 g) is then added. The solution is stirred and heated to about 60°–70° C. for about 15 min and then allowed to cool to 40°–45° C. To the reddish solution is added aqueous 7.5% $NH_4OH$ to a final pH between 9.5 and 10.0. A greenish suspension is produced which is subsequently heated to 95°–100° C. for 15 min. The resulting black suspension is then subjected to an ultrafiltration step using an Amicon RA 2000 hollow fiber dialysis unit equipped with a cartridge having a nominal cutoff of 100 kilodaltons. Light scattering measurements reveal that the product material has a volume median diameter of about 40 nm.

Next, to 25 mL of the above dispersion (40 mg Fe/mL) is added aqueous 25% gluteraldehyde (2.5 mL). The mixture is stirred overnight. Unreacted reagent is removed by dialysis against two changes of 20 liters of distilled water. A final volume of 35 mL of a dispersion containing 28.6 mg Fe/mL is obtained.

A 10 mL aliquot of the above-activated dispersion is treated with human transferrin (500 mg), and the resulting mixture is stirred overnight at room temperature. Unconjugated protein is separated by ultrafiltration as above using a 500 kilodalton-cutoff cartridge. A competitive-type radioimmunoassay revealed the presence of 160 μg transferrin per mg of dry superparamagnetic material.

6.6.3. Synthesis of Superparamagnetic Silane-Galactose Conjugate

A solution of 0.25M ferrous chloride and 0.5M ferric chloride (600 mL) is poured into a solution of 5M NaOH (600 mL). The black magnetic oxide precipitate which forms is repeatedly washed by base and decanted until a pH of about 9 is achieved.

In a beaker 400 mL of the magnetic oxide (about 15 grams) and 25 mL of glacial acetic acid is mixed. A sonic probe is placed in the beaker and the solution is sonicated at high intensity for 2 minutes. The sonic probe is then removed and 30 mL of N-2-aminoethyl-3-aminopropyltrimethoxysilane is added. The resulting mixture is then sonicated as before. The magnetic solution is subsequently added to 200 mL of glycerol at 50° C. The temperature is raised to 105° C. and the water is evaporated.

The resulting slurry is added to about 800 mL of water. Large aggregates of magnetic particles is removed by centrifuging the slurry at 1,000×g for 20 minutes. The supernatant is then dialyzed against citrate buffer in a hollow fiber dialysis device as in Example 6.6.2.

The glycerol dehydration step is adapted from U.S. Pat. No. 4,554,088 herein incorporated by reference.

To the resulting superparamagnetic silanized material is coupled galactose (lactose) groups by means known in the art for conjugating carbohydrate moieties to amine-containing groups. (See for example, Gray, G. R. *Arch. Biochem. Biophys.* 1974, 163, 426–428 and Section 6.3 substituting the silanized particles for BSA).

Another procedure for the conjugation step may be as follows:

To a stirred aqueous solution (50 mL) of lactose (10 g) is added 1-cyano-4-(dimethylamino)pyridinium tetrafluoroborate (10 mg) followed by 1 mL of an 0.2M aqueous solution of triethylamine. After 10 min, 10 mL of the silanized superparamagnetic material (13 mg/mL) is added. Stirring is allowed to continue overnight. The product is obtained after exhaustive dialysis against distilled water.

6.7. Biodistribution of Biodegradable Superparamagnetic RME-Type MR Contrast Agents The biodistribution of RME-type contrast agents may be determined by injecting them into vertebrate animals, sacrificing the animals after a short period of time, and determining the effect on the proton relaxation times of the tissues of interest. This general method can be illustrated for the case of MR contrast agents recognized and selectively internalized via galactose receptors of hepatocytes of the liver.

A Sprague Dawley rat is injected through the tail vein with an RME-type contrast agent (AsF/BSA) prepared according to Section 6.6.1 (2 mg Fe/kg of rat). After about 2 h, the animal is sacrificed and the liver and spleen are removed. Tissue samples from control animals and those injected with a superparamagnetic iron oxide (AMI-25, RES-type), or injected with a BSA-associated superparamagnetic iron oxide (RES-type), are obtained likewise. The $T_2$ proton relaxation times of the various tissues are determined using an IBM PC-20 pulsed MR spectrometer. The results are listed in Table II.

TABLE II

Proton Relaxation Times of Tissues Removed from Rats Used in Biodistribution Experiments[a]

| Contrast Agent | $T_2$ (msec) | | $1/T_2$ (sec$^{-1}$) | |
|---|---|---|---|---|
| | Liver | Spleen | Liver | Spleen |
| Normal | 36.5 | 65 | 27.4 | 15.4 |
| AsF/BSA[b] | 24 | 52 | 42.7 | 19.2 |
| AMI-25[c] | 11.7 | 16 | 85.5 | 62.5 |
| Normal | 32 | 48 | 31.3 | 20.8 |
| BSA[d] | 20 | 22 | 50.0 | 45.4 |

[a]Data from two sets of experiments are shown.
[b]RME-type contrast agent prepared according to Example 6.6.1. of the invention.
[c]Citrated superparamagnetic fluid prepared according to U.S. Application Serial No. 067,586.
[d]BSA superparamagnetic iron oxide complex prepared according to U.S. Pat. No. 4,770,183.

The results indicate that while the RES-type contrast agents (AMI-25 and BSA particle) dramatically affect the proton relaxation times of tissues derived from both the liver and spleen of treated rats, the RME-type contrast agent exhibits a marked preference for the liver tissue. Only slight changes in the proton relaxation rates are observed in the spleen of normal rats versus those administered with the RME-type contrast agent. These results demonstrate that the RME-type contrast agent prepared according to the invention and directed specifically to galactose receptor-bearing cells are taken up selectively in vivo by hepatocytes, which hepatocytes are found only in the liver tissue of animals and humans.

A distribution coefficient, D, can be defined by the expression written below (Eq. 1):

$$D = \frac{1/T_2 \text{ (treated liver)} - 1/T_2 \text{ (normal liver)}}{1/T_2 \text{ (treated spleen)} - 1/T_2 \text{ (normal spleen)}} \quad \text{(Eq. 1)}$$

in which $1/T_2$ is the relaxation rate obtained from the results of Table II. The magnitude of the term D provides an indication of the selectivity of a given RME-type MR agent for a given pair of tissues (i.e., the liver versus the spleen in the case supra). The larger the number the more selectively the agent is distributed in favor of one tissue. Table III lists the values of D calculated from the above-mentioned experiments, along with other pertinent information.

TABLE III

Distribution Coefficient, D, Calculated for Different Kinds of MR Contrast Agents

| Contrast Agent | D | Dose (mg Fe/kg rat) | Time$^a$ (h) | VMD$^b$ (nm) |
|---|---|---|---|---|
| AsF/BSA | 4.0 | 2 | 2 | 101 |
| AMI-25 | 1.23 | 2 | 1 | 70 |
| BSA | 0.76 | 2 | 1.5 | 100 |

$^a$Time elapsed after administration of contrast agent.
$^b$Volume median diameter obtained from light scattering method.

It is apparent from the data in Table III that the RES-type contrast agents (last two entries) do not manifest the type of selectivity enjoyed by the RME-type (first entry) agent of the present invention. The AsF/BSA particle is about 3 times more selective for the liver relative to AMI-25 and about 5 times more selective compared with a particle associated with BSA only. Depending upon the particular ligand being employed for targeting hepatocytes, the contrast agents of the instant invention can display D values of at least about 3 and even D values of at least about 20.

6.8. In Vivo MR Image Enhancement Using RME-Type Contrast Agents

An asialofetuin-associated (AsF) biodegradable superparamagnetic MR contrast agent is prepared according to Section 6.6.1. except that only asialofetuin (2.5 mg) is used in the synthesis.

A male Sprague-Dawley rat is anesthetized with sodium pentobarbital (40 mg/kg rat). The animal is then injected through the tail vein with a solution of the AsF particle (2 mg Fe/kg rat). The MR experiment was performed using a GE CSI MR instrument (45 cm bore, 2 Tesla). A variety of data-collection or post-accumulation data manipulation techniques may be used in the experiment including weighting schemes favoring $T_1$ and/or $T_2$, saturation recovery, spin echo, inversion recovery pulse sequences, or regions of interest (ROI) techniques (See, Stark, D. D. et al. Amer. J. Roentgen. 1985, 145, 213-220). In this example, a spin echo pulse sequence (TR, repetition time=500 msec; TE, echo time=30 msec) is used. A series of images is then generated which shows a significant darkening of the liver region below the lung (the lung is the black, bell-shaped area at T=0) after only 1 min after injection of the RME-type contrast agent (compare images at T=1, 15, and 30 min) indicating rapid and efficient liver uptake. The darkening effect diminishes over the next several days indicating rapid biodegradability.

6.9 Preparation of RME-Type MR Contrast Agents with Variable in Vivo Cell Surface Receptor Residence Times With the proper choice of ligand, RME-type contrast agents can be tailored to reside on the cell surface receptor for variable lengths of time before the onset of endocytosis. Thus, interferons are one group of proteins that enter cells much more slowly compared with other ligands such as epidermal growth factor (EGF), $\alpha_2$-macroglobulin ($\alpha_2$SM), or LDL (See Pastan and Willingham, TIBS 1983, Jul., 250-254).

The interferons (IFN) with free terminal amino groups are derivatized by reaction with p-nitrobenzoyl chloride in chloroform. The resulting p-nitrobenzoic acid amide of IFN is reduced to the p-amino derivative by treatment with sodium hydrosulfite in warm aqueous solution.

The p-aminophenylacetyl interferon (20 $\mu$mol) is dissolved in cold 2N HCl (0.2 mL) and diazotized by addition of ice-cold aqueous 0.1M sodium nitrite (0.2 mL). The mixture is allowed to stand at 4° C. for 10 min and then combined with an aqueous 0.5M sodium bicarbonate solution of BSA (34 mg, 2.0 mL). The pH of the mixture is raised to 8.5 by the dropwise addition of aqueous sodium carbonate. After stirring at 4° C. for 10 h, the mixture is dialyzed against distilled water and, if desired, lyophilized to yield the IFN-BSA conjugate as a powder.

The product IFN-BSA conjugate is labeled with superparamagnetic metal oxides as described in Section 6.6. These extended life time RME-type MR contrast agents may be especially useful in MR imaging experiments which require examinations over an extended period and may be conducted with fewer administrations of magnetic materials.

6.10. Hepatocyte Specific (HS) MR Contrast Agents

6.10.1. Preparation of Hepatocyte-Specific Colloidal Superparamagnetic Metal Oxide MR Contrast Agents An aqueous solution of trivalent and divalent metal salts is prepared as exemplified by the use of the following amounts of ferric and ferrous halide salts: FeCl$_3$ 6 H$_2$O (15.8 g, 58.5 mmol) and FeCl$_2$ 4H$_2$O (6.24 g, 31.6 mmol) are combined in distilled water (200 mL) and the resulting solution is then filtered through a 0.22 $\mu$m glass fiber filter to remove large debris. Equal volumes of this metal halide solution and a carbohydrate solution, prepared by dissolving arabinogalactan from larch wood (60 g, Sigma Chemical Co.) in distilled water (120 mL), are then combined at ambient temperature with vigorous stirring. To this mixture is then added, slowly and dropwise, a 30% aqueous ammonium hydroxide solution until the pH of the mixture reaches about 10. At this stage, the mixture is heated to a temperature about 90°-100° C. for about 15 minutes. The mixture is then allowed to cool with the formation of a black colloidal superparamagnetic iron oxide. The cooled mixture is then passed through a coarse glass fiber filter, followed by a series of Nalgene ® filters of decreasing porosity beginning with an 0.8 $\mu$m, then an 0.45 $\mu$m, and finally an 0.22 $\mu$m filter.

Excess arabinogalactan is then removed by ultrafiltration using a 2 liter hollow fiber dialysis unit having a 300 kilodalton molecular weight cutoff (Amicon Inc., Danvers, Mass.) as follows: the filtered product from the preceding step is loaded into the ultrafiltration unit, diluted and washed with 25 mM citrate buffer (pH 8.5). This washing step is repeated until a clear eluent is observed (about 5 cycles). The washed product is then concentrated to a final volume which is about equal to the initial volume of the combined metal salt and carbohydrate solutions. The final product, in which the yield based on iron is about 90%, is preferably refrigerated until needed.

6.10.2. Physical Characterization of the Hepatocyte-Specific MR Contrast Agent The size distribution of the final product, obtained by the procedure described in the preceding Section, may be determined in one of several ways. For example, and as mentioned previously in Section 6.6.1, light-scattering techniques offer a useful way of estimating the size distribution of a given sample. Electron microscopy (EM) is perhaps the preferred means for a reliable determination of the sizes and size distribution of suspended particles or colloids. It has been the experience of the present inventors that the volume median diameter (VMD, sometimes also referred to herein as the overall mean diameter), obtained from the light scattering experiments, is most closely correlated to the EM values.

Figure 2:
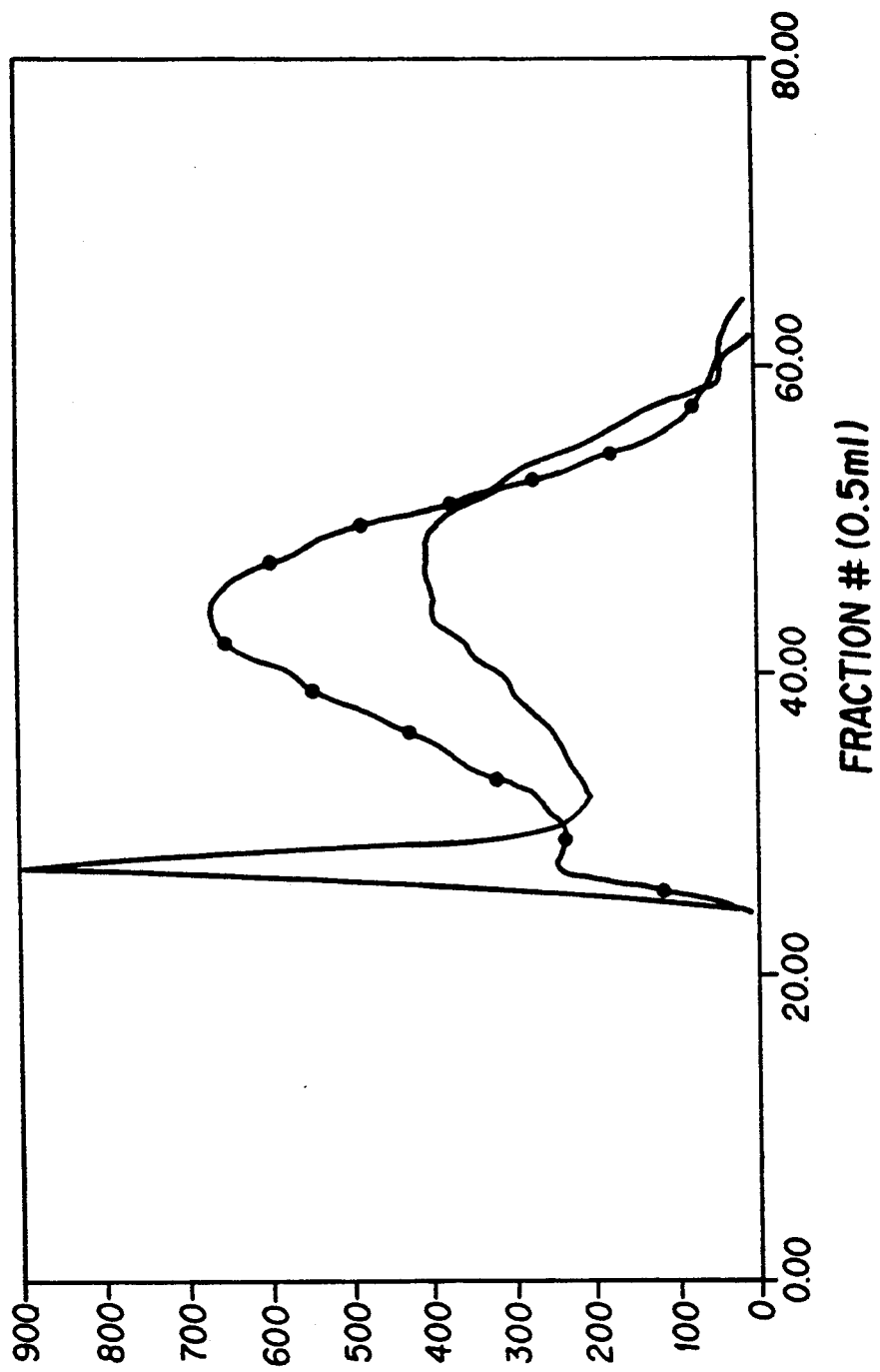
FIG. 2 shows the chromatogram obtained from a Sepharose 4B separation of the HS MR contrast agent (barbed line) and AMI-25 (solid line).

More conveniently, however, gel filtration chromatography, using, for example, Sepharose 4 B as the stationary phase, provides more than adequate quantitative determinations when the resulting fractions are correlated with samples of known size. In the present case, the final product is analyzed on a 100×0.3 cm Sepharose column. For comparative purposes, a sample of superparamagnetic metal oxide (AMI-25), prepared according to the methods described in U.S. Pat. No. 4,827,945, is analyzed similarly. The results are plotted in FIG. 2 (the solid line is the AMI-25 and the barbed line represents the size distribution of the HS MR contrast agent). The largest superparamagnetic particles are present in the early fractions, as exemplified by the excluded volume (fraction 28), and have been found, by light scattering, to have a VMD of about 120 nm. Ferritin, on the other hand, elutes with a peak at fraction 59 (not shown) close to the smallest of the superparamagnetic particles. This ferritin sample is known to have a diameter of about 10–15 nm by electron microscopy. One may conclude, therefore, that both the superparamagnetic particles prepared according to the previous methods, and the HS MR contrast agents of the present embodiments, have a size distribution between about 10 and about 120 nm. However, it is clear from FIG. 2 that the majority of HS MR contrast agent clusters are confined to a somewhat narrower and smaller size distribution relative to the superparamagnetic iron oxide (also referred to as "citrated") material. This difference in size and size distribution may be attributed to the additional heating step described in Section 6.10.1.

These two materials are subjected to further analyses including VMD determinations by light scattering methods (using an instrument, Model BI-90, available from Brookhaven Instruments, Inc., Ronkonkoma, N.Y.), their effects on proton relaxation times (using a PC-20 MR Spectrometer operating at 0.47 Tesla and available from IBM Instruments, Danbury, Conn.), and magnetic susceptibility as determined using a susceptibility balance (Johnson Matthey Inc., West Chester, Pa.). The results of these additional analyses are listed in Table IV.

TABLE IV

Physical Characteristics of a Colloidal Superparamagnetic HS MR Contrast Agent and a Citrated Superparamagnetic Reticuloendothelial System (RES)-Type MR Contrast Agent

| | MR Contrast Agent | |
|---|---|---|
| | HS | RES[d] |
| Size[a] (nm) | 54 | 72 |
| $R_1{}^b(M^{-b} sec^{-1})$ | $2.1 \times 10^4$ | $3 \times 10^4$ |
| $R_2{}^b(M^{-1} sec^{-1})$ | $5.2 \times 10^4$ | $10 \times 10^4$ |
| Magnetic Susceptibility[c] (c.g.s.) | $15.5 \times 10^3$ | $25.0 \times 10^{-3}$ |
| Surface Species | galactose | citrated |

[a]The size refers to the volume median diameter (overall mean diameter) as determined from light scattering methods of unfractionated material.
[b]$R_1$ and $R_2$ are the spin-lattice and spin-spin relaxivities which reflect the molar change in $1/T_1$ or $1/T_2$, produced by the MR contrast agents, respectively.
[c]The magnetic susceptibility is the weight susceptibility per gram of iron.
[d]The RES-type MR contrast agent (AMI-25) is prepared according to the methods described in U.S. Pat. No. 4,827,945.

6.11 In Vivo Results: Biodistribution and Pharmacokinetics of the HS MR Contrast Agents

6.11.1. Methods

One of two methods are used for administering the HS MR Contrast Agents and for anesthesizing the Sprague-Dawley rats (350 g, available from Charles River Labs, Wilmington, Mass.) used in these in vivo experiments. First, the rats ae anesthesized with an intraperitoneal injection of sodium pentabarbital (35 mg/kg dose). A lateral incision is made, and the HS MR contrast agent is injected into the vena cava. Blood samples are extracted from that vein. The data shown in FIG. 3 and Table V reflect the results obtained from this first method.

In the second method, a long acting anesthetic, Inactin (100 mg/kg dose), is injected intraperitoneally. The femoral artery and vein of the rats are then exposed by a small incision. The artery is then carefully separated from the vein. The HS MR Contrast Agent is subsequently injected into the femoral vein. For the blood lifetime studies, the artery is cannulated and 0.5 mL blood samples are then collected periodically.

The relaxation times are recorded at 38°±1° C. on the PC-20 MR instrument at 0.47 Tesla. $T_1$ is measured from eight data points generated with an inversion recovery pulse sequence. $T_2$ is measured from 10 data points with a Carr-Purcell-Meiboom-Gill pulse sequence (See, for example, Weissleder, R. W. et al. Amer. J. Roentgen. 1989, 152, 167–173; $T_1$ and $T_2$ are measured in this instrument as described therein).

MR images are obtained with a 2 Tesla GE CSI 45 cm bore unit with a time of repetition (TR) setting of 500 msec and a time to echo (TE) setting of 30 msec.

Also, the metal concentration of a given sample may also be measured, if desired, on an atomic absorption spectrophotometer, such as one manufactured by Perkin-Elmer Corp., Norwalk, Conn.), after dissolution of the metal oxide in 0.01 M HCl.

6.11.2. Results

Figure 3A:
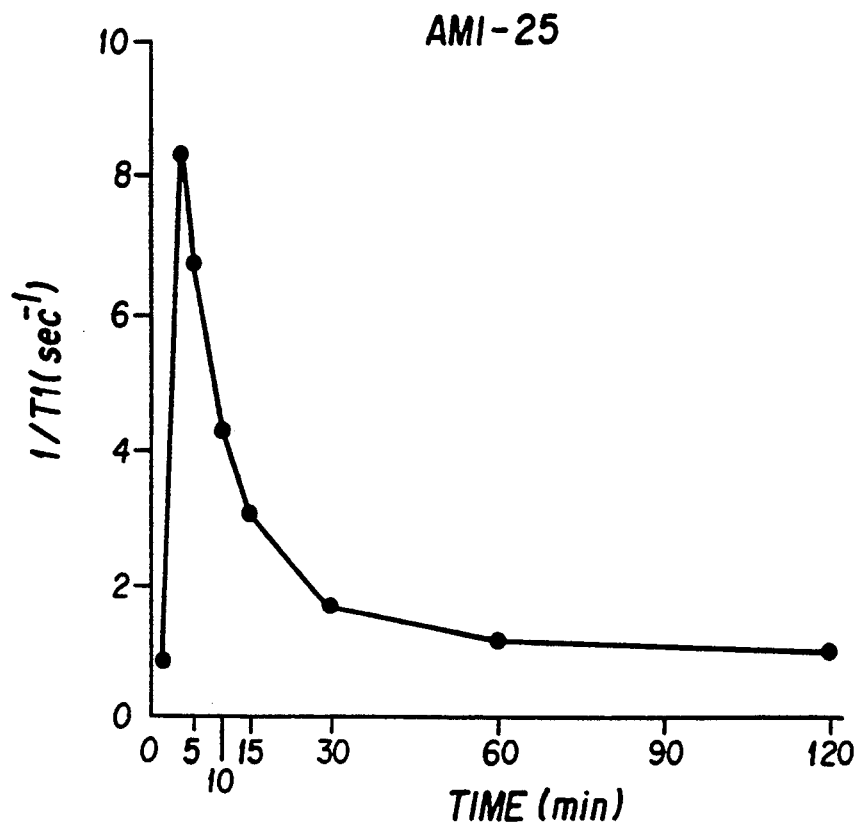
FIG. 3 shows the effects of administering RES-type (left) vs. HS-type (right) MR contrast agents on the blood relaxation rates of rats over time.
Figure 3B:
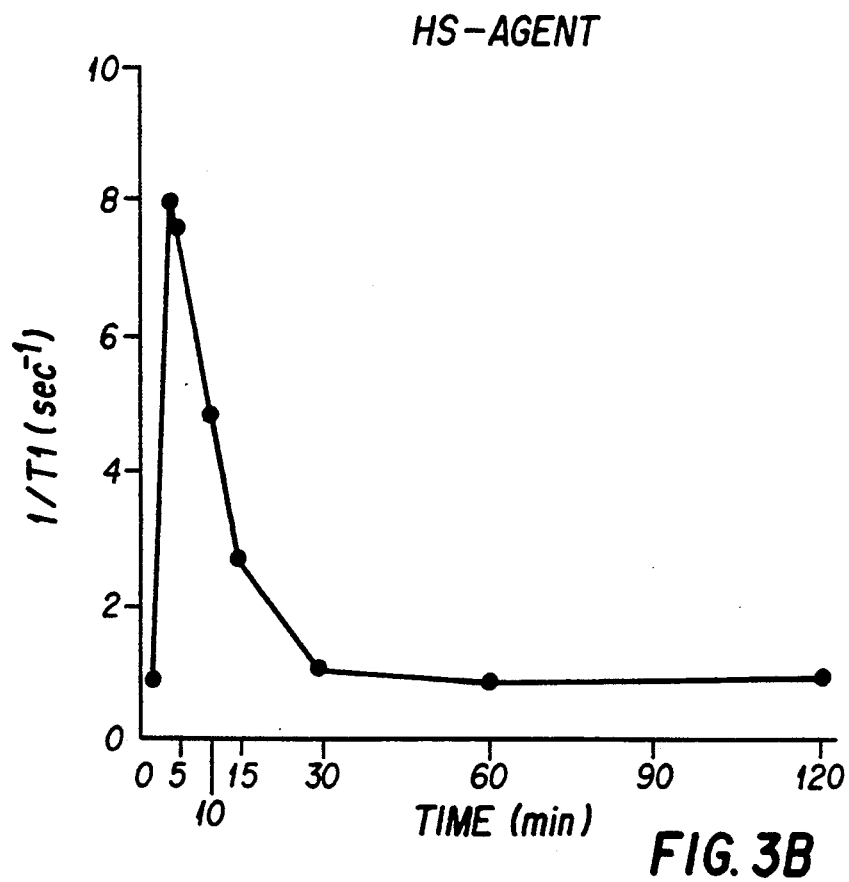

FIG. 3 shows the changes in blood spin-lattice relaxation rate ($1/T_1$) following the injection of 40 μmol/kg of either HS MR contrast agent or citrated RES-type MR contrast agent. The introduction of superparamagnetic colloids into blood produces a change in the blood relaxation rate which is proportional to the concentration of added superparamagnetic colloid over a wide concentration range; i.e., the change in $1/T_1$ is proportional to the blood concentration of the superparamagnetic colloid. All points in FIG. 3 are averaged over 6 rats. The blood half life is then calculated by fitting the data to a single exponential equation: $1/T_{1(t)} = 1/T_{1(base)} + Ae^{-kt}$. Here $1/T_{1(base)}$ and $1/T_{1(t)}$ are the spin-lattice relaxation rates of blood before injection of the superparamagnetic colloid or at some time (t) after injection. A is the concentration of the contrast agent in the blood at the moment of injection, and k is the rate constant for the decay of $1/T_1$ in the blood following injection. The blood half-life is then calculated from the value of k.

Employing the data shown in FIG. 3 and carrying the calculations through, the blood half-life for the HS MR contrast agent is 4.9 minutes (95% confidence limits). For the RES-type agent, a blood half-life of 6.4 minutes is obtained (95% confidence limits). Thus, both contrast agents are rapidly cleared from the blood. Blood half-lives based on measurements of $1/T_2$, are calculated in a similar fashion and are found to be 3.9 min and 6.7 min for the HS and RES-type MR contrast agents, respectively.

A hepatocyte directable or hepatocyte specific MR contrast agent should ideally be cleared from blood only by the liver, the source of hepatocytes, while other superparamagnetic RES-type MR contrast agents, like AMI-25, are cleared from the blood by the phagocytic action of the RES (e.g., Kupffer cells of the liver). In rats, radiotracer studies indicate that the highest concentration of AMI-25 is found in the spleen (See, for example, Weissleder, R. W. et al. *Amer. J. Roentgen.* 1989, 152, 167–173).

The hepatic and splenic relaxation rates ($1/T_1$'s and $1/T_2$'s) resulting from the injection of 20 μmol/kg of either the HS MR agent or AMI-25 are shown in Table V. All animals are sacrificed 60 minutes after injection of the contrast agent. The HS MR agent caused large changes in the relaxation rates of the liver, without causing a significant change in the splenic values of $1/T_1$ and $1/T_2$. As expected, the RES-Type MR agent, AMI-25, produced large changes in the relaxation rates of both the liver and the spleen.

The ratio of hepatic uptake to splenic uptake provides a simple measure of the degree of hepatocyte specificity of the HS agent. Using Eq. 1 (Section 6.7), the distribution coefficient, D, is readily calculated for the HS RES-type MR contrast agents. For the HS MR contrast agent a value of 30.9 is obtained confirming the high degree of specificity of the HS MR contrast agent for the hepatocytes of the liver over splenic tissue. In this set of experiments, a value of 0.82 is found for AMI-25, actually indicating a preference by the RES-type MR contrast agent for the spleen. It is worth noting that the difference between this D value (0.82) and that obtained in Table III (1.23) for AMI-25 may indicate a certain intrinsic variability in biodistribution studies of mice particularly where dosages and modes of anesthesia are different. However, this slight variability in no way defeats the surprising specificity data obtained for the HS MR contrast agent, which data are obtained under substantially the same experimental conditions as the contemporaneous set of AMI-25 studies.

TABLE V

| Changes in Tissue Relaxation Rates, Superparamagnetic HS Versus RES-Type MR Contrast Agents | | | |
|---|---|---|---|
| | Baseline | HS MR Agent | AMI-25 |
| liver | | | |

TABLE V-continued

| Changes in Tissue Relaxation Rates, Superparamagnetic HS Versus RES-Type MR Contrast Agents | | | |
|---|---|---|---|
| | Baseline | HS MR Agent | AMI-25 |
| $1/T_1$ | 3.44 | 5.14 | 4.37 |
| S.D. | 0.32 | 0.33 | 0.22 |
| n | 13 | 8 | 12 |
| spleen | | | |
| $1/T_1$ | 1.65 | 1.73 | 3.14 |
| S.D. | 0.12 | 0.1 | 0.38 |
| n | 13 | 6 | 12 |
| liver | | | |
| $1/T_2$ | 22.4 | 53.4 | 33.6 |
| S.D. | 1.7 | 6.3 | 3.0 |
| n | 13 | 8 | 12 |
| spleen | | | |
| $1/T_2$ | 16.2 | 17.3 | 29.8 |
| S.D. | 1.3 | 2.1 | 3.3 |
| n | 13 | 6 | 12 |

Figure 4:
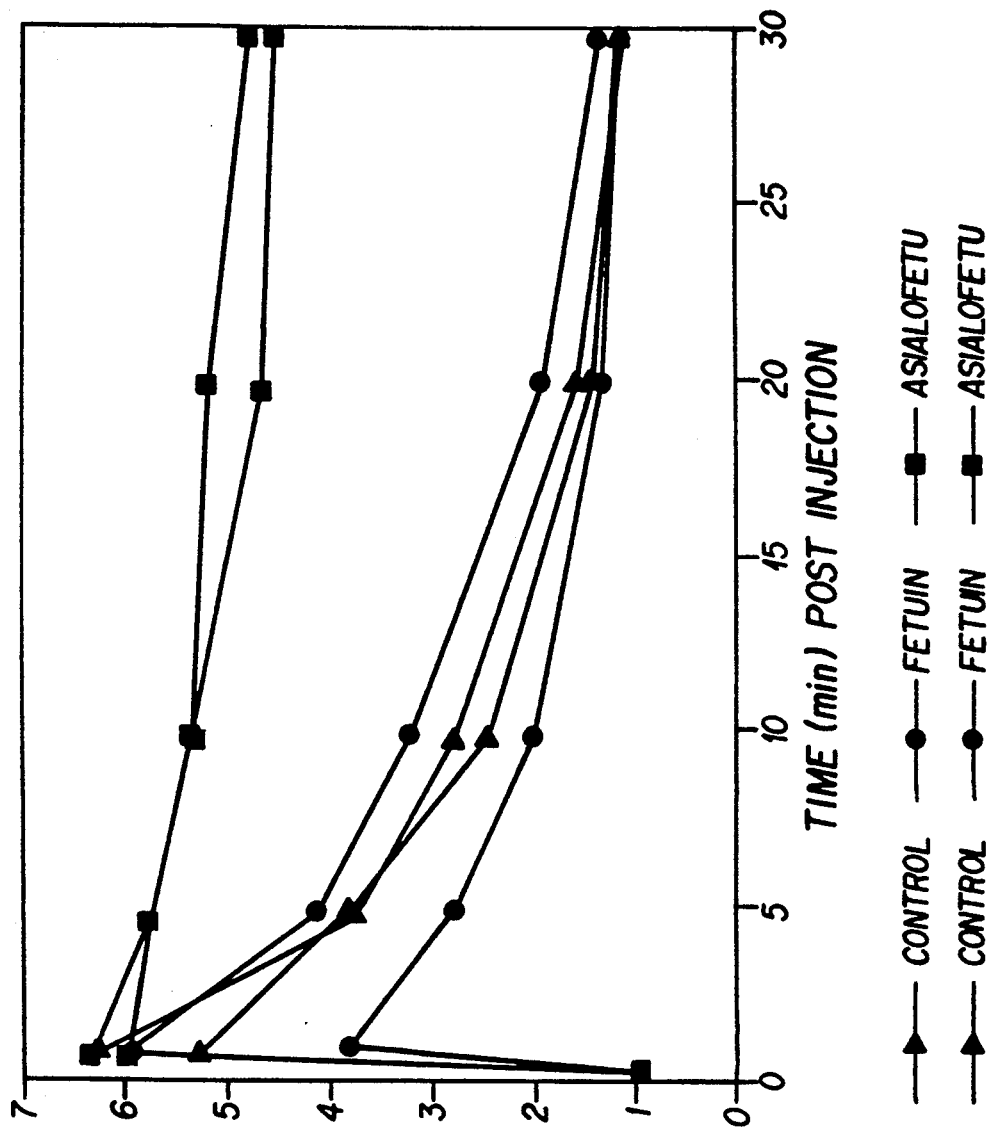
FIG. 4 shows the effect of co-injected glycoproteins on the clearance of the HS MR contrast agent from the blood of rats: $\Delta$, no co-injected glycoproteins; +, co-injected with fetuin; $\square$, co-injected with asialofetuin.

6.12. Action of the Asialogylcoprotein Receptor in Clearing HS MR Contrast Agents from the Blood If a superparamagnetic iron oxide colloid is cleared from the blood via the asialoglycoprotein receptor, the presence of circulating asialoglycoproteins should retard its removal from the blood. To examine this hypothesis, two rats are injected with asialofetuin (100 mg/kg), two more rats with fetuin (100 mg/kg), and yet another two rats serve as a control and are not injected with glycoprotein. After allowing 5 minutes for dilution of each protein in the vascular compartment, 20 μmol/kg of the HS MR contrast agent is injected into all six animals. FIG. 4 shows the changes in blood $1/T_1$ for each group of rats. The increase in $1/T_1$ produced by the HS MR contrast agent is clearly greatly prolonged by injection of asialofetuin into rats, thus confirming the intermediacy of the asialoglycoprotein receptor in the cellular mechanism for clearing the HS MR contrast agent from the vascular compartment.

This result also demonstrates the utility of employing co-injected or pre-injected asialoglycoproteins for inhibiting the removal of the HS MR contrast agent by the capillary bed (the so-called "first pass extraction efficiency") and increasing the likelihood of obtaining useful and meaningful information about the metabolic state of the liver hepatocytes.

Figure 5:
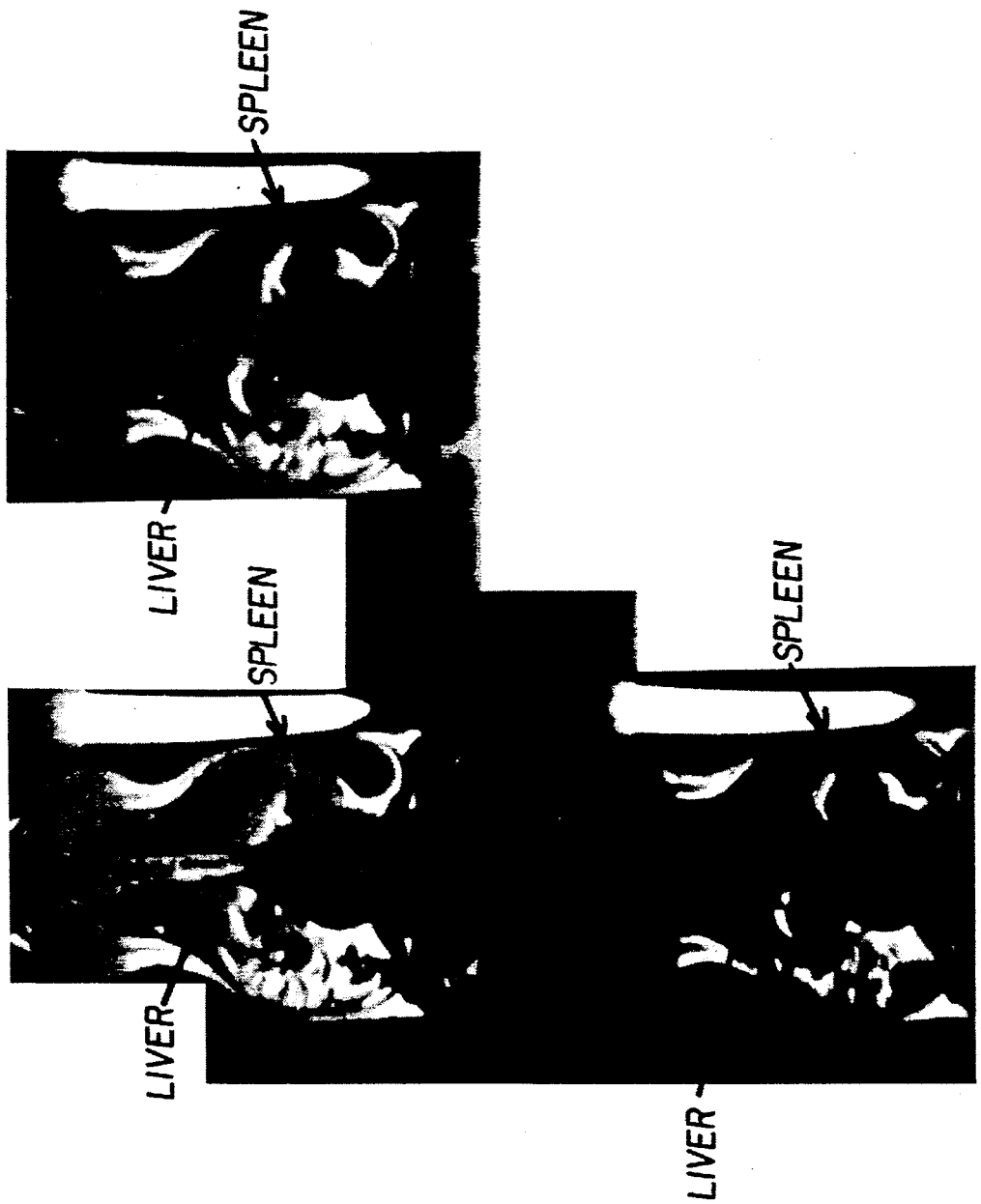
FIG. 5 shows MR image of a rat before administration of contrast agent (upper left), after administration of 20 $\mu$mol/kg HS MR contrast agent (upper right), and after co-administration of 20 $\mu$mol/kg HS and 100 $\mu$mol/kg AMI-25 MR contrast agents (lower left).

6.13. MR Images Produced by Administration of the HS MR Contrast Agents of the Present Invention Finally the HS MR contrast agent is examined for its efficacy as an MR contrast agent. The top right image of FIG. 5 shows a coronal image of an uninjected rat, while the top left image is taken about 15 minutes after the injection of 20 μmol Fe/kg of the HS MR contrast agent. The plane of the coronal images is chosen to permit visualization of both the liver and the spleen. After injection of the HS MR contrast agent the liver darkens (upper left) dramatically, but there is a lack of darkening of the spleen (lower right, as defined by the arrow). the bottom image shows that a darkened spleen does obtain when the same rat is injected with 100 μmol Fe/kg of the RES-type MR contrast agent, AMI-25. By both tissue relaxation rate data (Table V), or MR imaging (FIG. 5), the HS MR contrast agent produces dramatic effects on liver but not splenic relaxation rates.

6.14. Toxicology

It has been found that the injection of 1800 μmol Fe/kg fails to produce any adverse effects in rats over the standard observation period of 48 hours. This dose corresponds to about 90 times the imaging dose used in FIG. 5 (20 μmol/kg). The safety factor for the HS MR agent, i.e., $LD_{50}$/imaging dose, is, therefore, at least 90.

6.15. Preparation of Labeled Arabinogalactan

Like other carbohydrates which have been derivatized in the prior art, arabinogalactan is modified to incorporate metal chelating groups like DTPA as described, for example, by Jacobson et al. in European Patent Application Nos. 0184899 and 0186947. The complete disclosures of both published applications are incorporated herein, by reference. After modification of the carbohydrate to include a chelating group, a solution of a paramagnetic metal salt is then introduced to the modified carbohydrate to provide the arabinogalactan species labeled with a paramagnetic metal. Suitable metals include, but are not limited to paramagnetic iron, gadolinium, or radioactive metal isotopes including gallium-67, technetium-99, or technetium-99m. Others, which may also be desirable, are readily apparent to those of ordinary skill in the art.

Moreover, techniques are known by which other radioisotope tracers are incorporated into carbohydrate species. For example, Bolton and Hunter describes a procedure which employs a phenolic acylating agent which functions in a similar way to DTPA anhydride (See, *Biochem J.* 1973, 133, 529–539, the disclosure of which is incorporated herein by reference). Upon acylation of the carbohydrate, in this case arabinogalactan, a chloramine T iodination reaction is carried out, as described by Greenwood and Hunter (*Ibid*, 1963, 89, 114–123, the disclosure of which is incorporated herein by reference), by which any isotope of iodine may be introduced, but especially iodine-123 or the equivalent iodine-125.

It should be apparent that other modifications and embodiments can be contemplated without departing significantly from the scope and spirit of the present invention. The invention should, therefore, not be limited by the foregoing examples and descriptions thereof but only as enumerated in the following claims.

What is claimed is:

1. A method for obtaining an enhanced MR image of an organ or tissue of an animal or human subject which comprises:
   (a) administering to such a subject an effective amount of a colloidal biodegradable superparamagnetic contrast agent in a physiologically acceptable medium such that an image-enhancing amount of such contrast agent can be internalized by hepatocytes of the liver by receptor mediated endocytosis, said contrast agent comprising (1) biodegradable superparamagnetic metal oxide particles, physically or chemically joined with (2) a ligand, wherein such metal oxide particles;
   comprise one or more individual biodegradable superparamagnetic metal oxide crystals, and are capable of being biodegraded in such subject, as evidenced by a return of proton relaxation rates of the liver to preadministration levels, within 30 days of administration; and
   wherein such ligand:
   comprises a terminal galactose moiety, is recognized and internalized, thereby permitting said metal oxide particles to be internalized, by hepatocytes of the liver by receptor mediated endocytosis, and
   is selected from the group consisting of (i) a glycoprotein and (ii) a macromolecular species conjugate, which macromolecular species conjugate comprises two macromolecular species, a first macromolecular species which is a glycoprotein and a second macromolecular species which is physically or chemically joined with the metal oxide particles and conjugated to the first macromolecular species; and
   (b) recording such MR image.

2. The method according to claim 1 in which said ligand is asialofetuin in combination with other serum proteins.

3. The method according to claim 1 in which said contrast agent is employed in combination with a receptor-blocking agent.

4. The method according to claim 1 in which said metal oxide particles have an overall mean diameter of about 2000 angstroms or less, as measured by light scattering.

5. The method according to claim 4 in which said metal oxide particles have an overall mean diameter of about 1000 angstroms or less, as measured by light scattering.

6. The method according to claim 1 in which said ligand is a glycoprotein selected from the group consisting of asialofetuin, asialoorosomucoid and a neoglycoalbumin.

7. The method according to claim 1 in which said ligand is a macromolecular species conjugate, the first macromolecular species of which is a glycoprotein selected from the group consisting of asialofetuin, asialoorosomucoid and a neoglycoalbumin.

8. The method according to claim 1 or 7 in which the second macromolecular species of the macromolecular species conjugate is a carbohydrate.

9. The method according to claim 8 in which said carbohydrate is dextran.

10. The method according to claim 1 or 7 in which the second macromolecular species of the macromolecular species conjugate is an organosilane.

11. The method according to claim 10 in which said organosilane is selected from the group consisting of 3-aminopropyltrimethoxysilane, p-aminophenyltrimethoxysilane, N-2-aminoethyl-3-aminopropyltrimethoxysilane, n-dodecyltriethoxysilane, and n-hexyltrimethoxysilane.

12. A method for diagnosing the metabolic state of the liver of a human or animal subject, which method comprises:
   (a) recording a series of MR images of the liver according to the method of claim 1; and
   (b) comparing said images obtained in step (a) in order to determine the degree of internalization of said contrast agent by hepatocytes of the liver, as well as the metabolic state of the liver.

13. The method according to claim 1 in which the metal of said metal oxide particles is iron.

14. a colloidal biodegradable superparamagnetic contrast agent, said contrast agent comprising (i) biodegradable superparamagnetic metal oxide particles, physically or chemically joined with (2) a ligand,
   wherein such metal oxide particles:

comprise one or more individual biodegradable superparamagnetic metal oxide crystals, and are capable of being biodegraded in such subject, as evidenced by a return of proton relaxation rates of the liver to preadministration levels, within 30 days of administration; and wherein such ligand:

comprises a terminal galactose moiety, is recognized and internalized, thereby permitting said metal oxide particles to be internalized, by hepatocytes of the liver by receptor mediated endocytosis, and is selected from the group consisting of (i) a glycoprotein and (ii) a macromolecular species conjugate, which macromolecular species conjugate comprises two macromolecular species, a first macromolecular species which is a glycoprotein and a second macromolecular species which is physically or chemically joined with the metal oxide particles and conjugated to the first macromolecular species.

15. The composition according to claim 14 in which the metal of said metal oxide particles is iron.

16. The composition according to claim 15 in which galactose/iron molar ratio is not less than about 0.0001 and not greater than about 1.0.

17. The composition according to claim 14 which is further characterized as having a distribution coefficient, D, favoring the hepatocytes of the liver over a reference organ or tissue of at least about 3.

18. the composition according to claim 14 which is further characterized as having a distribution coefficient, D, favoring the hepatocytes of the liver over a reference organ or tissue of at least about 20.

19. The composition according to claim 14 in which said particles have an overall mean diameter of about 2000 angstroms or less, as measured by light scattering.

20. The composition according to claim 14 in which said particles have an overall mean diameter of about 1000 angstroms or less, as measured by light scattering.

21. The composition according to claim 14 in which said ligand is a glycoprotein selected from the group consisting of asialofetuin, asialoorosomucoid and a neoglycoalbumin.

22. The composition according to claim 14 in which said ligand is a macromolecular species conjugate, the first macromolecular species of which is selected from the group consisting of asialofetuin, asialoorosomucoid and a neoglycoalbumin.

23. The composition according to claim 14 or 22 in which the second macromolecular species of the macromolecular species conjugate is a carbohydrate.

24. The composition according to claim 23 in which said carbohydrate is dextran.

25. The composition according to 14 or 22 in which the second macromolecular species of the macromolecular species conjugate is an organosilane.

26. The composition according to claim 25 in which said organosilane is selected from the group consisting of 3-aminopropyltrimethoxysilane, p-aminophenyltrimethoxysilane, N-2-aminoethyl-3-aminopropyltrimethoxysilane, n-dodecyltriethoxysilane, and n-hexyltrimethoxysilane.

27. The method according to claim 12 in which the metal of said metal oxide particles is iron.

* * * * *